US006670138B2

(12) United States Patent
Gonzalez-Zulueta et al.

(10) Patent No.: US 6,670,138 B2
(45) Date of Patent: Dec. 30, 2003

(54) METHOD OF DIAGNOSING ISCHEMIC STROKE VIA UCP-2 DETECTION

(75) Inventors: Mirella Gonzalez-Zulueta, Pacifica, CA (US); Mehrdad Shamloo, San Mateo, CA (US); K.C. McFarland, Davis, CA (US); Daniel Chin, Foster City, CA (US); Tadeusz Wieloch, Lund (SE); Thorsten Melcher, San Francisco, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 10/001,051

(22) Filed: Oct. 31, 2001

(65) Prior Publication Data

US 2002/0172958 A1 Nov. 21, 2002

Related U.S. Application Data

(60) Provisional application No. 60/244,946, filed on Nov. 1, 2000, now abandoned.

(51) Int. Cl.[7] ............................. C12Q 1/70; C12Q 1/68; G01N 33/53; A61K 39/395; C07K 7/00

(52) U.S. Cl. ................................ 435/7.1; 435/5; 435/6; 435/7.92; 424/130.1; 530/300; 530/350

(58) Field of Search .................................. 530/300, 330; 424/130.1; 435/7.92, 6, 7.1, 5

(56) References Cited

U.S. PATENT DOCUMENTS

| 6,001,578 A | * | 12/1999 | Lind et al. ...................... 435/6 |
| 6,365,796 B1 | * | 4/2002 | Lowell et al. ................. 800/3 |
| 6,384,087 B1 | * | 5/2002 | Zemel et al. ............... 514/909 |

FOREIGN PATENT DOCUMENTS

| WO | WO96/05861 | 2/1996 |
| WO | WO99/48905 | 9/1999 |
| WO | WO 99/53953 | 10/1999 |
| WO | WO00/06087 | 2/2000 |
| WO | WO 00 17353 | 3/2000 |

OTHER PUBLICATIONS

Chavin et al. (Feb. 26, 1999) "Obesity Induces Expression of Uncoupling Protein–2 in Hepatocytes and Promotes Liver ATP Depletion." Journal of Biological Chemistry 274(9): 5692–5700.*
Campbell et al. (Jan. 1999) "Association between a marker in the UCP–2/UCP–3 gene cluster and genetic susceptibility to anorexia nervosa." Molecular Psychiatry 4(1): 68–70.*
Fukunaga et al. (Sep. 2000) "Altered gene expression of uncoupling protein–2 and –3 in stroke–prone spontaneous hypertensive rats." Journal of Hypertension 18(9): 1233–1238.*
Mattiasson et al. (2003) "Uncoupling protein–2 prevents neuronal death and diminishes brain dysfunction after stroke and brain trauma." Nature Medicine Advance Online Publication: 1–7.*
Yoshida et al. (May 2002) "Monitoring changes in gene expression in renal ischemia–reperfusion in the rat." Kidney Internationa 61(5): 1646–1654.*
Mattson and Liu (May 9, 2003) "Mitochondrial potasssium channels and uncoupling proteins in synaptic plasticity and neuronal cell death." Biochemical and Biophysical Research Communications 304(3): 539–549.*
Horvath et al., "UCP2 in neurons and glia following brain and spinal cord injury," Society for Neuroscience Abstracts, (2000), vol. 26: 1–2.
Pitkanen et al., "Prevention of neuronal cell death by anticonvulsants in experimental epilepsy (extended abstract)," ACTA Neurologica Scandinavica, (1995), vol. 162: pp. 22–23.
Raghupathi et al., "Apoptosis after traumatic brain injury," Journal of Neurotrauma, (2000), vol. 17: 10, pp. 927–938.
Bouillaud F. et al., "Complete cDNA–derived amino acid sequence of rat brown fat uncoupling protein", (1986), J. Biol. Chem., 261(4):1487–90.
Klingenberg M. et al., "The uncoupling protein dimer can form a disulfide cross–link between the mobile C–terminal SH groups", (1989), Eur. J. Biochem., 180(1):123–31.
Rial E. et al., "Retinoids activate proton transport by the uncoupling proteins UCP1 and UCP2", EMBO, (1999), vol. 18(21):5827–33.
Diehl AM, Hoek JB., *Mitochondrial uncoupling: role of uncoupling protein anion carriers and relationship to thermogenesis and weight control "the benefits of losing control"*, (1999), J. Bioenerg Biomembr, 31(5):493–506.
Jezek P., *Fatty acid interaction with mitochondrial uncoupling proteins*, (1999), J. of Bioenergetics and Biomembranes, 31(5):457–66.
Klingenberg M., *Uncoupling proteins—A Useful Energy Dissipator*[1], J. of Bioenergetics and Biomembranes, (1999), 31(5):419–430.

(List continued on next page.)

Primary Examiner—Elizabeth Kemmerer
Assistant Examiner—Christopher James Nichols
(74) Attorney, Agent, or Firm—Pamela J. Sherwood; Bozicevic, Field & Francis LLP; Rebecca D. Taylor

(57) ABSTRACT

The present invention identifies a gene whose gene product provides a protective effect against neurological disorders or neuronal injuries. Further, the invention provides methods for diagnosing or assessing an individual's susceptibility to a neuronal injury such as stroke. Also provided are therapeutic methods for treating patients, and methods for prophylactically treating individuals susceptible to various neurological disorders or neuronal injuries. Additionally, the invention describes screening methods for identifying agents that can be administered to treat individuals that have suffered or are at risk to suffer such disorders or injuries.

8 Claims, 10 Drawing Sheets

OTHER PUBLICATIONS

Matthias A, Ohlson KB, Frederiksson JM, Jacobsson A, Nedergaard J, Cannon B., *Thermogenic responses in brown fat cells are fully UCP1–dependent UCP2 or UCP3 do not substitute for UCP1 in adrenergically or fatty scid–induced thermogenesis*, (2000), J. Biol. Chem., 275(33):25073–81.

Muzzin P, Boss O, Giacobino JP., *Uncoupling protein 3: its possible biological role and mode of regulation in rodents and humans*, (1999), J. Bioenerg. Biomembr., 31(5):467–73.

Nedergaard J, Matthias A, Golozoubova V, Asadi A, Jacobsson A, Cannon B., *UCP1: The Original Uncoupling Protein–and Perhaps the Only One?*, (1999), J. of Bioenergetics and Biomembranes, 31(5):475–491.

Nicholls DG, Rial E., *A history of the first uncoupling protein, UCP1*, (1999), J. Bioenerg. Biomembr., 31(5)399–406.

Ricquier D, Bouillaud F., *The uncoupling protein homologues: UCP1, UCP2, UCP3, StUCP and AtUCP*, (2000), Biochem. J., 345 Pt 2:161–79.

Ricquier D, Miroux B, Cassard–Doulcier AM, Levi–Meyrueis C, Gelly C, Raimbault S, Bouillaud F., *Contribution to the identification and analysis of the mitochondrial uncoupling proteins*, (1999), J. Bioenerg. Biomembr., 31(5):407–18.

Stuart JA, Brindle KM, Harper JA, Brand MD., *Mitochondrial proton leak and the uncoupling proteins*, J. Bioenerg. Biomembr., (1999), 31(5):517–25.

Wojtczak L, Wieckowski MR., *The mechanisms of fatty acid–induced proton permeability of the inner mitochondrial membrane*, J. Bioenerg. Biomembr., (1999), 31(5):447–55.

Boss et al., "Uncoupling protein–3: a new member of the mitochondrial carrier family with tissue–specific expression", FEBS Letters, 1997, p. 39–42, vol. 408.

Fleury et al., "Uncoupling protein–2: a novel gene linked to obesity and hyperinsulinemia", Nat. Genet., 1997, p. 269–272, vol. 15.

Gimeno et al., "Cloning and Characterization of an Uncoupling Protein Homolog A Potential Molecular Mediator of Human Thermogenesis", Diabetes, 1997, p. 900–906, vol. 46.

* cited by examiner

METHOD OF DIAGNOSING ISCHEMIC STROKE VIA UCP-2 DETECTION

CROSS-REFERENCE TO RELATED APPLICATIONS

This application claims the benefit of priority from U.S. Provisional Patent Application Serial No. 60/244,946, filed Nov. 1, 2000 now abandoned, the full disclosures of which are incorporated herein by reference in their entirety for all purposes.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present invention relates to methods for diagnosing or assessing an individual's susceptibility to a neurological disorder or a neuronal injury. The invention also relates to therapeutic methods for treating an individual suffering from a neurological disorder or a neuronal injury and methods for identifying agents that can be administered to treat such an individual.

BACKGROUND OF THE INVENTION

Uncoupling proteins (UCPs; thermogenins) are proton-translocating proteins located in the inner mitochondrial membrane that play a role in metabolic processes, particularly non-shivering thermogenesis. The first UCP (UCP-1) was found to be localized in the brown adipose tissue, specialized fat cells that function in heat generation and energy balance. Hibernating and cold-adapted animals have significant stores of such tissue. The evidence indicates that UCPs function to maintain the core body temperature of hibernating mammals and other cold-adapted animals by raising the resting metabolic rate of the animals (see, e.g., Nicolls, D. G. and Locke, R. M. (1984) Physiol. Rev. 64:2–40; and Rothwell, N.J., and Stock, M. J. (1979) Nature 281:31–35).

As the name indicates, UCPs serve an uncoupling function, specifically by uncoupling proton flux through the mitochondrial membranes and ATP synthesis. The mitochondrial oxidation of metabolites (e.g., pyravate and fatty acids) is accompanied by proton transport out of the mitochondrial matrix, thereby generating a transmembrane proton gradient. The protons re-enter the mitochondria through the protein ATP synthase and drive the synthesis of ATP. The UCPs, however, provide a route for the re-entry of the protons that is uncoupled to ATP synthesis. Consequently, instead of the proton gradient resulting in the generation of ATP, UCPs act to covert the proton gradient into heat energy and increase the rate of respiration. Exposure to the cold triggers the neural and hormonal stimulation of brown adipose tissue, which in turn increases UCP-mediated proton transport and heat production (see, e.g., Susulic, V. S., and Lowell, B. B. (1996) Curr. Opin. in Endocrinol. and Meta. 3:44–50). Studies conducted with various transgenic models have demonstrated that a reduction in UCP activity correlates with the development of obesity and diabetes (see, e.g., Lowell, B. B., et al. (1993) Nature 366:740; and Kopecky, J. et al. (1995) J. Clin. Invest. 96:2914–23).

While humans have a UCP-1 gene that is active in brown fat, these fat deposits disappear shortly after birth (see, e.g., Bouillaud, et al. (1985) Proc. Natl. Acad. Sci. 82:445–448). Nonetheless, measurements showing that 25% to 30% of the oxygen that humans and other animals utilize to metabolize their food is used to compensate for mitochondrial proton leaks suggested the presence of other UCPs in humans. In fact, several human UCPs have now been identified.

One such UCP is referred to in the literature as UCP-2 or UCPH. The gene encoding this protein maps to human chromosome 11 and has been linked to hyperinsulinemia and obesity. UCP-2 is reported to be expressed in various adult tissue, including brain, muscle and fat cells (see, e.g., Fleury, et al. (1997) Nat. Genet. 15:269–272; Tartaglia, et al. PCT Publication No. WO 96/05861; Gimeno, et al. (1997) Diabetes 46:900–906; and Boss, et al. (1997) FEBS Letters 408:39–42). Allelic variants of UCP-2 appear to have been identified. While some UCP-2 proteins have an alanine at position 55 (see, Fleury, supra, and PCT Publication No. WO 00/06087), other UCP-2 proteins have a valine (see, PCT Publication WO 96/05861). At position 219, some UCP-2 proteins have a threonine (see, PCT Publication WO 96/05861 and PCT Publication WO 00/06087), whereas other UCP-2 proteins have an isoleucine (see, Fleury, supra). Methods for screening for allelic variants are discussed in PCT Publication WO 99/48905.

A third human UCP (UCP-3) has also been recently reported. This UCP is preferentially expressed in human skeletal muscle. The gene encoding this particular UCP maps to human chromosome 11, adjacent to the gene for UCP-2. Studies indicate that UCP-3 expression can be regulated by known thermogenic stimuli such as leptin, β-adrenergic agonists and thyroid hormone (see, e.g., PCT publication WO 98/45313; Boss, et al., (1997) FEBS Letters 408:39–42; Vidal-Puig, et al. (1997) J. Biol. Chem. 272:24129–24132; Solanes et al. (1997) J. Biol. Chem. 272:25433–25436; and Gong, et al. (1997) J. Biol. Chem. 272:24129–24312).

A fourth human UCP (UCP-4) has been identified. This UCP is expressed in a number of different tissues including, brain, heart, pancreas and muscle tissue (see, e.g., PCT Publication WO 00/04037). Another human UCP (UCP5/BMCP1) is most abundantly expressed in the brain, and at lower levels in most peripheral organs (Sanchis, et al. (1998) J. Biol. Chem. 273: 36411, and PCT Publication WO 00/032624).

Because of the role UCPs play in uncoupling the oxidation of metabolites and the storage of the resulting energy in the form of ATP, UCPs have been viewed primarily as targets for controlling a number of weight disorders (e.g., obesity and underweight disorders), as well as related diseases (e.g., diabetes). However, there is a paucity of information regarding other physiological functions of UCP and how UCP can be utilized in other types of applications other than weight-related applications.

SUMMARY OF THE INVENTION

Provided herein are various methods for diagnosing and treating various neurological disorders and neuronal injuries, particularly stroke and ischemic stroke. Methods for screening agents to identify agents useful in treating neurological disorders and injuries are also provided.

More specifically, certain methods involve diagnosing the occurrence of a stroke or assessing a patient's susceptibility to a stroke by detecting in a patient sample an elevated level of UCP-2 expression. In some methods, detection is accomplished by detecting elevated levels of UCP-2 transcript. Other methods involve detecting an elevated level of UCP-2 polypeptide. Elevated levels of UCP-2 polypeptide can be detected using various immunological techniques such as ELISA assays.

Some of the diagnostic methods provided herein involve assessing a patient's risk of having a stroke. Such methods involve comparing the level of UCP-2 expression in a test sample from the patient with a baseline value, wherein an elevated level of UCP-2 expression in the patient sample relative to the baseline indicates that the patient is at risk for stroke. A variety of baseline levels can be utilized in these methods. In some instances the baseline is the level of UCP-2 expression in a patient sample obtained previously. In other methods, the baseline value is an average value, a mean value or another statistical value for a population of control individuals.

Certain treatment methods provided herein involve treating a subject having or being susceptible to a neurological disorder or a neuronal injury by administering to the subject an effective amount of an agent that increases the activity of UCP-2. The neurological disorders or neuronal injuries that are amenable to the methods include stroke, Parkinson's disease, Huntington's disease, inherited ataxias, motor neuron diseases, Alzheimer's disease, epilepsy and traumatic brain injury. If the subject is susceptible to the neurological disorder or the neuronal injury, the subject is administered a prophylactic amount of the agent prior to occurring of the disorder or the injury. If, however, the subject has already suffered the neurological disorder or the neuronal injury, then the subject is administered a therapeutic amount of the agent. The agent which increases the activity of UCP-2 can be co-administered with various other agents, including, for example, agents that increase permeability of the blood/brain barrier and/or blood anticoagulants. In certain treatment methods, the agent is a purified UCP-2 polypeptide administered with a pharmaceutically acceptable carrier.

Certain treatment methods involve administering agents that stimulate the synthesis or expression of UCP-2 or a UCP-2 inducing agent. In some methods, the agent administered is a nucleic acid that encodes UCP-2 or a UCP-2 inducer. In such instances, the nucleic acid can be inserted into a viral vector or other expression vectors. The viral vector can also include a promoter operably linked to the nucleic acid which selectively drives expression in nerve cells. The promoter can be a UCP-2 promoter or a heterologous promoter. In certain methods, the viral vector is introduced into the cerebrospinal fluid; in other methods, the vector is injected into the intraventricular space. Still other treatment methods also involve producing ex vivo genetically-modified neuronal or non-neuronal stem cells that harbor the vector that includes a nucleic acid encoding UCP-2. The modified stem cells are then introduced into the intracerebroventricular space or into the cerebrospinal fluid.

A variety of screening methods is provided. Certain of these methods involve screening for an agent useful for treating a neuronal injury (e.g., stroke, traumatic brain injury) or a neurological disorder (e.g., Parkinson's disease, Alzheimer's disease, or epilepsy) by identifying an agent that upregulates UCP-2 expression and/or activity. Some of the screening methods involve: (a) administering to a test subject a test compound, wherein the test subject is a mammal other than a human; (b) preconditioning the test subject; and (c) determining in a sample from the test subject the expression level of UCP-2 to identify a test agent that upregulates UCP-2 expression in the test subject.

In other screening methods, agents useful for treating a neurological disorder or a neuronal injury are identified by identifying an agent that inhibits cellular apoptosis. Often such methods are conducted to identify agents useful in treating stroke or ischemic stroke. Certain screens identify compounds that inhibit the loss of mitochondrial membrane potential. Other screens provided herein identify agents that inhibit opening of the mitochondrial transition pore and release of cytochrome c from mitochondria and/or agents that inhibit the activation of caspases, as these events are associated with cellular apoptosis.

BRIEF DESCRIPTION OF THE DRAWINGS

FIG. 1A shows that UCP-2 expression is low in the CA1 under normal conditions. FIG. 1B illustrates the increase in UCP-2 mRNA levels at two days following a 3 minute ischemic event. FIG. 1C shows that there is no increase in UCP-2 mRNA levels at one day of recovery after a 10 minute ischemic insult. FIG. 1D shows that UCP-2 mRNA levels are increased at 24 h after 3 minutes of ischemic preconditioning prior to the 10 minute ischemic insult (3 min–24 h–10 min–24 h-in situ).

FIG. 6A is a plot of cell death for uninfected cells (No Ad), control cells infected with an adenovirus bearing the lacZ gene (Ad.LacZ) instead of the UCP-2 gene or test cells infected with an adenovirus having the UCP-2 gene (Ad.UCP2). Tests were conducted either without OGD (open boxes) or 90 minutes of OGD (darkened boxes). FIG. 6B shows the extent of cell death for cell cultures not subjected to OGD (control) and cell cultures exposed to 10 min OGD, 90 min OGD or 10 minute of OGD preconditioning followed by 90 min of OGD.

DETAILED DESCRIPTION

I. Definitions

Figure 1:
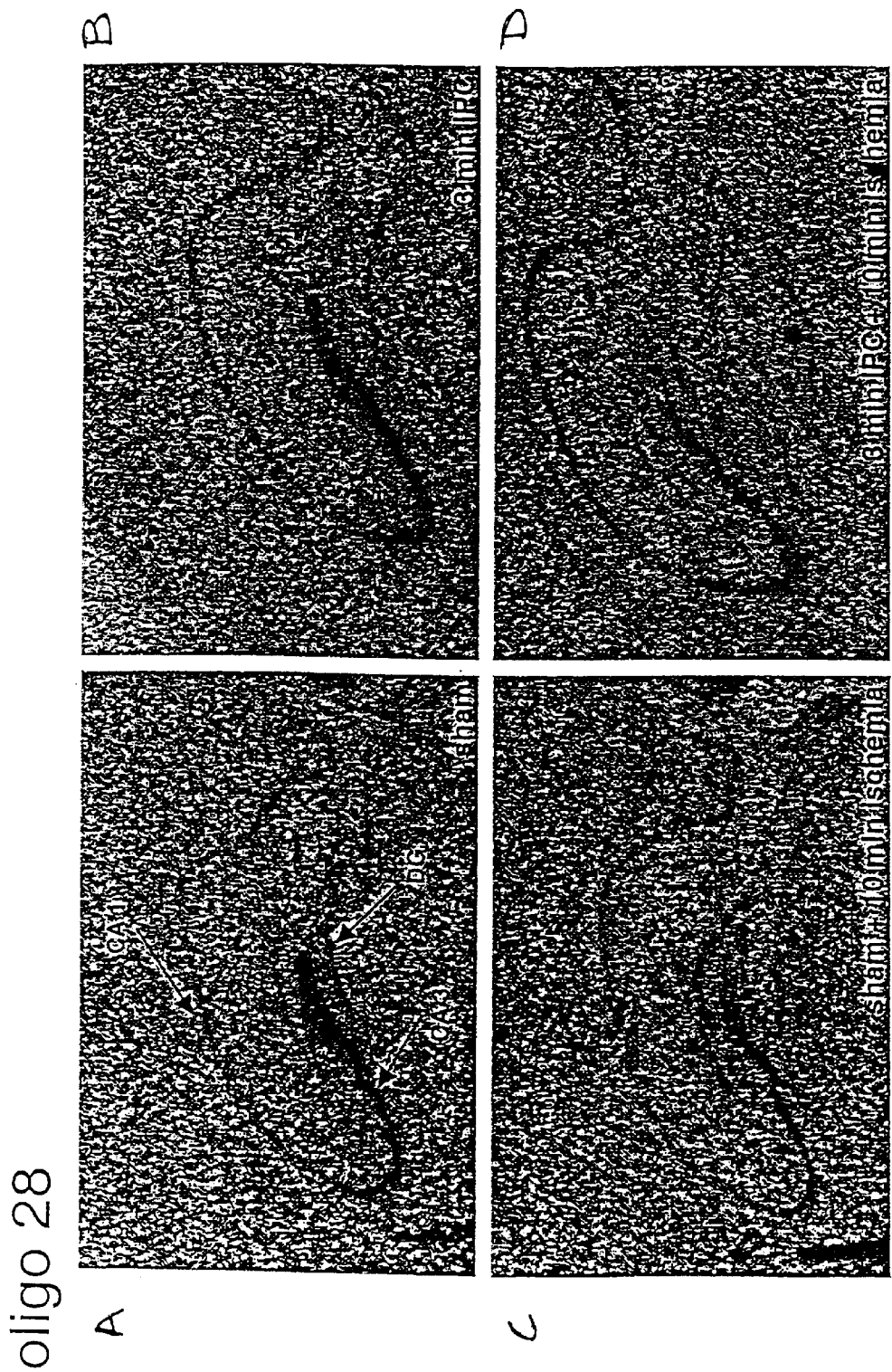
FIGS. 1A–1D are photomicrographs showing the results of in-situ hybridization experiments conducted with brain sections obtained from rats subjected to various treatment protocols which show the regions of the brain in which UCP-2 mRNA is localized. In particular, the photographs show the localization of a labeled probe (oligo 28) that specifically hybridizes with UCP-2 at the CA1, CA3 and DG regions of the rat brain hippocampus.

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

Various biochemical and molecular biology methods are well known in the art. For example, methods of isolation and purification of nucleic acids are described in detail in WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993); Chapter 3 of Laboratory Techniques in Biochemistry and Molecular Biology: Hybridization With Nucleic Acid Probes, Part 1. Theory and Nucleic Acid Preparation, (P. Tijssen, ed.) Elsevier, N.Y. (1993); and Sambrook et al., Molecular Cloning: A Laboratory Manual, Cold Spring Harbor Press, N.Y., (1989); Current Protocols in Molecular Biology, (Ausubel, F. M. et al., eds.) John Wiley & Sons, Inc., New York (1987–1993). Large numbers of tissue samples can be readily processed using techniques known in the art, including, for example, the single-step RNA isolation process of Chomczynski, P. described in U.S. Pat. No. 4,843,155.

A variety of methods are known for amplifying nucleic acids. Examples of suitable amplification techniques include, but are not limited to: (1) the polymerase chain reaction (PCR) [see, e.g., PCR Technology: Principles and Applications for DNA Amplification (H. A. Erlich, Ed.) Freeman Press, NY, N.Y. (1992); PCR Protocols: A Guide to Methods and Applications (Innis, et al., Eds.) Academic Press, San Diego, Calif. (1990); and U.S. Pat. Nos. 4,683,202 and 4,683,195]; (2) the ligase chain reaction (LCR) [see, e.g., Wu and Wallace, Genomics 4:560 (1989) and Landegren et al., Science 241:1077 (1988)]; (3) transcription amplification [see, e.g., Kwoh et al., Proc. Natl. Acad. Sci. USA 86:1173 (1989)]; (4) self-sustained sequence replication [see, e.g., Guatelli et al., Proc. Natl. Acad. Sci. USA, 87:1874 (1990)]; and, (5) nucleic acid based sequence amplification (NABSA) [see, e.g., Sooknanan, R. and Malek, L., BioTechnology 13: 563–65 (1995)].

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, in certain embodiments these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels that are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates), and with positively charged linkages (e.g., aminoalklyphosphoramidates, aminoalkyl-phosphotriesters), those containing pendant moieties, such as, for example, proteins (including nucleases, toxins, antibodies, signal peptides, poly-L-lysine), those with intercalators (e.g., acridine, psoralen), those containing chelators (e.g., metals, radioactive metals, boron, oxidative metals), those containing alkylators, those with modified linkages (e.g., alpha anomeric nucleic acids), as well as unmodified forms of the polynucleotide or oligonucleotide. In particular, DNA is deoxyribonucleic acid.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14–25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding UCP-2) and a promoter. Additional factors necessary or helpful in effecting expression can also be used as described herein. For example, transcription termination signals, enhancers, and other nucleic acid sequences that influence gene expression, can also be included in an expression cassette.

The term "stringent conditions" refers to conditions under which a probe or primer will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. In other instances, stringent conditions are chosen to be about 20° C. or 25° C. below the melting temperature of the sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) Methods in Enzymology, vol. 152: Guide to Molecular Cloning Techniques, San Diego: Academic Press, Inc. and Sambrook et al. (1989) Molecular Cloning: A Laboratory Manual, 2nd ed., vols. 1–3, Cold Spring Harbor Laboratory), both incorporated herein by reference. As indicated by standard references, a simple estimate of the $T_m$ value can be calculated by the equation: $T_m=81.5+0.41(\% \text{ G+C})$, when a nucleic acid is in aqueous solution at 1 M NaCl (see e.g., Anderson and Young, "Quantitative Filter Hybridization," in *Nucleic Acid Hybridization* (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions can also be achieved with the addition of destabilizing agents such as formamide.

The term "expression" when used in the context of expression or a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

The terms "upregulated and "activation" when used in reference to the expression of a nucleic acid such as a gene (particularly UCP-2) refers to any process which results in an increase in production of a gene product. A gene product can be either RNA (including, but not limited to, mRNA, rRNA, tRNA, and structural RNA) or protein. Accordingly, gene upregulation or activation includes those processes that increase transcription of a gene and/or translation of a mRNA. Examples of gene upregulation or activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene upregulation or activation can constitute, for example, inhibition of repression as well as stimulation of expression above an existing level. Examples of gene upregulation or activation processes that increase translation include those that increase translational initiation, those that increase translational elongation and those that increase mRNA stability.

The level of gene expression, including the level of gene activation or upregulation, can be quantitated utilizing a number of established techniques including, but not limited to, Northern-Blots, RNase protection assays (RPA), nucleic acid probe arrays, quantitative PCR (e.g., the so-called TaqMan assays), dot blot assays and in-situ hybridization. These are described further infra.

In general, gene upregulation or activation comprises any detectable increase in the production of a gene product, preferably an increase in production of a gene product by at least 50 to 100%, in other instances from about 2- to about 5-fold or any integer therebetween, in still other instances between about 5- and about 10-fold or any integer therebetween, sometimes between about 10- and about 20-fold or any integer therebetween, in other instances between about 20- and about 50-fold or any integer therebetween, in yet other instances between about 50- and about 100-fold or any integer therebetween, and in still other instances 100-fold or more. The terms upregulated and gene activation can also mean that the observed activity relative to a baseline level is a is a statistically significant difference (i.e., increase).

As used herein a "baseline value" generally refers to a value (or ranges of values) against which an experimental or determined value (e.g., one determined for a patient sample as part of a diagnostic or prognostic test) is compared. Thus, in the case of UCP-2 upregulation, the baseline value can be a value for UCP-2 activity or expression for a sample obtained from the same individual at a different time point. In other instances, the baseline value is a value determined for a control cell or individual, or a statistical value (e.g., an average or mean) established for a population of control cells or individuals. In the specific instance of UCP-2 upregulation, the control can be a cell, individual or populations thereof for which UCP-2 levels would not be expected to be upregulated. Thus, for instance, a control individual or control population can include healthy individuals, particularly those that have not suffered a stroke or those not susceptible to stroke. The population that serves as a control can vary in size, having as few as a single member, but potentially including tens, hundreds, thousands, tens of thousands or more individuals. When the control is a large population, the baseline value can be a statistical value determined from individual values for each member or a value determined from the control population as an aggregate (e.g., a value measured for a population of cells within a well).

A difference is typically considered to be "statistically significant" if the probability of the observed difference occurring by chance (the p-value) is less than some predetermined level. As used herein a "statistically significant difference" refers to a p-value that is <0.05, preferably <0.01 and most preferably <0.001. Typically, the upregulation of UCP-2 is at least 20%, in still other instances at least 40% or 50%, in yet other instances at least 70% or 80%, and in other instances at least 90% or 100%, although the change can be considerably higher.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

For the sake of simplicity, as used herein, the term "UCP-2 polypeptide," "UCP-2 protein" or simply "UCP-2" refers to a protein having a native UCP-2 amino acid sequence, as well as variants and modified forms regardless of origin or mode of preparation. The UCP-2 protein can be from any animal source, typically a mammalian source, most typically a human. A UCP-2 protein having a native amino acid sequence is a protein having the same amino acid sequence as a UCP-2 as obtained from nature (i.e., a naturally occurring UCP-2). Such native sequence UCP-2 proteins can be isolated from nature or can be prepared using standard recombinant and/or synthetic methods. Native sequence UCP-2 proteins specifically encompass naturally occurring truncated or soluble forms, naturally occurring variant forms (e.g., alternatively spliced forms), naturally occurring allelic variants of UCP-2 and forms including postranslational modifications. One specific example of a native sequence of UCP-2 is the full-length native sequence UCP-2 comprising the amino acid residues set forth as SEQ ID NO:2 (Genbank U76367), as reported by Fleury et al. (1997) Nature Genetics 15:269–272, which is incorporated by reference in its entirety. This protein is encoded by the a nucleic acid having the sequence set forth in SEQ ID NO:1. Other native sequence UCP-2 proteins have the same sequence as set forth in SEQ ID NO:2, except that amino residue 55 is valine instead of alanine (see, Tartaglia, et al., PCT Publication No. WO 96/05861, which is incorporated by reference) and/or amino acid residue 219 is threonine instead of isoleucine (see, Tartaglia, supra, and Chen, et al., PCT Publication WO 00/06087, which is incorporated by reference). A native sequence UCP-2 protein includes proteins following post-translational modifications such as glycosylation of certain amino acid residues.

UCP-2 variants refer to proteins that are functional equivalents to a native sequence UCP-2 protein that have similar amino acid sequences and retain, to some extent, one of the UCP-2 activities. Variants also include fragments that retain UCP-2 activity. UCP-2 activities include, but are not limited to, uncoupling activity and immunological cross-reactivity with antibodies that specifically bind to native sequence UCP-2. Preferred functional equivalents retain all of the activities of UCP-2, although the activity of such equivalent proteins can be stronger or weaker when compared on a quantitative basis. Typically, functional equivalents have activities that are within 1% to 10,000% of the activity of a native sequence UCP-2, while other functional equivalents have activities that are 10% to 1000%, or 50% to 500% of that of a native sequence UCP-2.

Variants also include proteins that are substantially identical to a native sequence UCP-2. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence UCP-2 (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. (1986) Nucl. Acids Res. 13:4331; Zoller et al. (1987) Nucl. Acids Res. 10:6487), cassette mutagenesis (Wells et al. (1985) Gene 34:315), restriction selection mutagenesis (Wells, et al. (1986) Philos. Trans. R. Soc. London SerA 317:415), and PCR mutagenesis (Sambrook, et al. (1989) Molecular Cloning, Cold Spring Harbor Laboratory Press).

Modified forms of UCP-2 generally refer to proteins in which one or more amino acids of a native sequence UCP-2 have been altered to a non-naturally occurring amino acid residue. Such modifications can occur during or after translation and include, but are not limited to, phosphorylation, glycosylation, cross-linking, acylation and proteolytic cleavage.

In view of the foregoing, references to a "UCP-2 nucleic acid" includes nucleic acids that encode for the various UCP-2 proteins described supra. The UCP-2 nucleic acids include nucleic acids (e.g., DNA and RNA) that are complementary to the coding sequences. Given the degeneracy of the genetic code, UCP-2 nucleotides also include all degenerate sequences that encode for the UCP-2 proteins as defined supra.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher nucleotide or amino acid residue identity, when compared and aligned for maximum correspondence, as measured using a sequence comparison algorithm such as those described below for example, or by visual inspection. Preferably, the substantial identity exists over a region of the sequences that is at least about 40–60 residues in length, preferably over a longer region than 60–80 amino acids, more preferably at least about 90–100 residues, and most preferably the sequences are substantially identical over the full length of the sequences being compared, such as the coding region of a nucleotide for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987–1999, including supplements such as supplement 46 (April 1999)]. Use of these programs to conduct sequence comparisons are typically conducted using the default parameters specific for each program.

Another example of algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

A further indication that two nucleic acid sequences or polypeptides are substantially identical is that the polypeptide encoded by the first nucleic acid is immunologically cross reactive with the polypeptide encoded by the second nucleic acid, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

The term "antibody" as used herein includes antibodies obtained from both polyclonal and monoclonal preparations, as well as the following: (i) hybrid (chimeric) antibody molecules (see, for example, Winter et al. (1991) *Nature* 349:293–299; and U.S. Pat. No. 4,816,567); (ii) F(ab')$_2$ and F(ab) fragments; (iii) Fv molecules (noncovalent heterodimers, see, for example, Inbar et al. (1972) Proc. Natl. Acad. Sci. USA 69:2659–2662; and Ehrlich et al. (1980) Biochem 19:4091–4096); (iv) single-chain Fv molecules (sFv) (see, for example, Huston et al. (1988) Proc. Natl. Acad. Sci. USA 85:5879–5883); (v) dimeric and trimeric antibody fragment constructs; (vi) humanized antibody molecules (see, for example, Riechmann et al. (1988) Nature 332:323–327; Verhoeyan et al. (1988) Science 239:1534–1536; and U.K. Patent Publication No. GB 2,276, 169, published Sep. 21, 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579–1584; Cumber et al. (1992) J. Immunology 149B:120–126); and, (vii) any functional fragments obtained from such molecules, wherein such fragments retain specific-binding properties of the parent antibody molecule.

The phrases "specifically binds" when referring to a protein, "specifically immunologically cross reactive with," or simply "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ M$^{-1}$ or $10^4$ M$^{-1}$, sometimes $10^5$ M$^{-1}$ or $10^6$ M$^{-1}$, in other instances $10^6$ M$^{-1}$ or $10^7$ M$^{-1}$, preferably $10^8$ M$^{-1}$ to $10^9$ M$^{-1}$, and more preferably, about $10^{10}$ M$^{-1}$ to $10^{11}$ M$^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

The term "isolated," "purified" or "substantially pure" means an object species (e.g., a UCP-2 protein or nucleic acid) is the predominant macromolecular species present (i.e., on a molar basis it is more abundant than any other individual species in the composition), and preferably the object species comprises at least about 50 percent (on a molar basis) of all macromolecular species present. Generally, an isolated, purified or substantially pure UCP-2 protein or nucleic acid will comprise more than 80 to 90 percent of all macromolecular species present in a composition. Most preferably, the object species is purified to essential homogeneity (i.e., contaminant species cannot be detected in the composition by conventional detection methods) wherein the composition consists essentially of a single macromolecular species.

The term "naturally occurring" as applied to an object means that the object can be found in nature.

The term "neurological disorder," "neurological injury," or "neuronal injury" generally refers to a disorder associated with some type of injury to neuronal cells or the death of neuronal death. Specific examples of such disorders include, but are not limited to, stroke, ischemic stroke, Parkinson's disease, Huntington's disease, inherited ataxias, motor neuron diseases, Alzheimer's disease, epilepsy, and traumatic brain injury.

The term "apoptosis" has its general meaning in the art and refers to the process by which cells undergo a process of programmed cell death. Activation of caspase 3 is a marker for apoptosis. Apoptosis, including increased caspase 3 activity, has been implicated in various neurological disorders or neuronal injuries, e.g., stroke (Rosenblum, Stroke, 30: 1154–6; 1999; MacManus et al., J Neurotrauma, 17: 899–914, 2000; and Guglielmo et al., Neurol Res, 20: 283–96, 1998), traumatic brain injury (Raghupathi et al., J Neurotrauma, 17: 927–38, 2000), epilepsy (Timsit et al., Eur J Neurosci, 11: 263–78, 1999; and PitkAnen et al., Acta Neurol Scand Suppl, 162: 22–3, 1995), Parkinson's disease (Ziv et al., Mov Disord, 13: 865–70, 1998; and Tatton, Exp Neurol, 166: 29–43, 2000), and Alzheimer's disease (Hugon et al., J Neural Transm Suppl, 59: 125–31, 2000; and Masumura et al., Brain Res Mol Brain Res, 80: 219–27, 2000).

As used herein the term "stroke" has the meaning normally accepted in the art. The term can broadly refer to the development of neurological deficits associated with impaired blood flow regardless of cause. Potential causes include, but are not limited to, thrombosis, hemorrhage and embolism. The term "ischemic stroke" refers more specifically to a type of stroke that is of limited extent and caused due to blockage of blood flow.

A "tissue" refers to an aggregation of similar cells united in performance of a particular function. The tissue can be part of a living organism, a section excised from a living organism, or can be artificial. An artificial tissue is one in which the aggregation of cells are grown to function similar to a tissue in a living organism. The aggregated cells, however, are not obtained from a host (i.e., a living organism). Artificial tissues can be grown in vivo or in vitro.

The term "detectably labeled" means that an agent (e.g., a probe) has been conjugated with a label that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

II. Overview

A variety of methods for diagnosing and treating individuals that have either suffered a neurological injury, that are at risk for neurological injury, or that have a neurological disorder are provided. High throughput screening methods to identify compounds effective in treating such individuals are also provided, as are compositions that include compounds identified through such screening methods. The methods and compositions find utility with a variety of neurological disorders, including stroke and, more specifically, ischemic stroke. The methods are based in part upon the finding that UCP-2 is differentially expressed (upregulated) in an ischemic preconditioning model in rat, indicating that UCP-2 exerts a protective effect against various neurological disorders, particularly stroke.

Certain methods are also based upon evidence indicating that UCP-2 inhibits certain components of an apoptotic cascade (see, e.g., Example 4). More specifically, the evidence indicates that UCP-2 may interfere with the effects of mitochondrial $Ca^{2+}$ accumulation and the subsequent mitochondrial permeability transition (see, e.g., Example 4). Mitochondria have a large capacity for buffering $Ca^{2+}$, and during various toxic stimuli mitochondria accumulate large quantities of $Ca^{2+}$. However, excessive mitochondrial $Ca^{2+}$ overload interfere with mitochondrial ATP production and lead to opening of the permeability transition pore (PTP). The PTP is a voltage-sensitive proteinaceous pore that allows solutes of <1,500 Daltons to equilibrate across the membrane (see D. G. Nicholls and S. L. Budd (2000) Physiological Reviews 80: 315–361). Opening of the pore results in dissipation of the mitochondrial membrane potential and mitochondrial swelling. Mitochondrial swelling induces release of cytochrome c into the cytosol where it interacts with apoptotic mediators. Pore formation can be inhibited, amongst other factors, by low matrix pH. UCP-2 is a mitochondrial proton transporter that leaks protons into the mitochondrial matrix. Thus, while not intending to be bound by any particular theory, it may be that activation of UCP-2 leads to a decreased matrix pH and subsequent prevention of PTP opening.

In view of the increase in UCP-2 expression observed in response to a neurological insult, the diagnostic and prognostic methods generally involve detecting the occurrence of a stroke or assessing an individual's susceptibility to stroke by detecting an elevated level of UCP-2 expression or activity in a sample obtained from the patient. Because of the protective effect provided by UCP-2, both therapeutic and prophylactic treatment methods for individuals suffering or at risk of a neurological disorder such as stroke involve administering either a therapeutic or prophylactic amount of an agent that increases the activity of UCP-2. The agent that acts to increase UCP-2 activity can be a purified form of UCP-2, an agent that stimulates expression or synthesis of UCP-2, or a nucleic acid that includes a segment encoding UCP-2, or any agent that acts as an activator of the UCP-2 activity and function including but not limited to pharmacological agonists, or partial agonists. In view of the role of UCP-2 role as a potential regulator of mitochondrial permeability transition and release of cytochrome c, as well as an inhibitor of caspase-3 activation, the agent can also be one that has similar effects on PTP, cytochrome c release and caspase-3 activation.

The screening methods generally involve conducting various types of assays to identify agents that upregulate the expression or activity of UCP-2. Such screening methods can initially involve screens to identify compounds that can bind to UCP-2. Certain assays are designed to measure more clearly the effect that different agents have on UCP-2 activities or expression levels. Other screening methods are designed to identify compounds that influence mitochondrial permeability transition and inhibit caspase-3 activation as does UCP-2. Lead compounds identified during these screens can serve as the basis for the synthesis of more active analogs. Lead compounds and/or active analogs generated therefrom can be formulated into pharmaceutical compositions effective in treating neurological disorders such as stroke.

III. Differential Expression of UCP-2

The mammalian brain has a limited capacity to survive long periods of hypoxia and ischemia (lack of oxygen and blood supply). Following exposure to hypoxia-ischemia, neurons die by rapid or slow mechanisms of cell death (necrosis or apoptosis). Hypoxic-ischemic brain insults, such as stroke, neonatal asphyxia, heart failure (prolonged lack of blood supply to the brain), or drowning, can cause severe permanent brain damage.

On the other hand, brief, sublethal periods of hypoxia-ischemia can lead to a transient phase in the brain when neurons become protected from subsequent injury and death. This treatment, generally referred to as ischemic tolerance, or ischemic preconditioning, can provide the basis for and lead to an understanding of intrinsic protective mechanisms and pathways through endogenous proteins or factors that provide for this effect. Thus, as used herein, ischemic preconditioning refers to a brief, transient, non-destructive stroke that triggers intrinsic neuroprotective mechanisms.

Stroke can be modeled in animals, such as the rat, by occluding certain cerebral arteries that prevent blood from flowing into particular regions of the brain, then releasing the occlusion and permitting blood to flow back into that region of the brain (reperfusion). These focal ischemia models are different than global ischemia models where blood flow to the entire brain is blocked for a period of time prior to reperfusion. Certain regions of the brain are particularly sensitive to this type of global ischemic insult. The hippocampus, and more specifically the CA1 region of the hippocampus, is primarily affected by global ischemia. Ten minutes of global ischemia induce profound selective neuronal loss in the CA1 region of hippocampus with non-detectable neuronal damage in CA3 region and dentate gyrus of hippocampus. With increasing periods of global ischemia, delayed cell death can also be detected in the striatum and layers 2 and 5 of the cerebral cortex (Lipton (1999) Physiol. Rev. 79: 1431–1568). In contrast, in focal ischemia, the precise region that is directly damaged is dictated by the location of the blockade and duration of ischemia prior to reperfusion. In animal models of focal ischemia there is, like in the human condition, a gradation of ischemia from the infarct core of the lesion to the outermost boundary, and hence there are different metabolic conditions within the affected site. Because of its duration and heterogeneity, the insult is complex.

In the rat, ten minutes global ischemia (Two-Vessel occlusion model with hypotension, Lipton (1999) Physiol. Rev. 79: 1431–1568) is sufficient to induce the complete destruction of CA1 neurons in the hippocampus. However, a three-minute ischemic event and several hours of recovery time are sufficient to effectively reduce the damage of a ten-minute ischemic insult. This neuroprotective effect is dependent on de novo protein synthesis. Therefore, genes that are specifically upregulated in an ischemic preconditioning model may be neuroprotective, either directly or indirectly, whereas longer ischemic times may lead to the induction of other genes that have neuro-damaging properties. The rat model of both ischemic preconditioning and global ischemia is highly relevant because it duplicates the ischemia/reperfusion that occurs in the human brain during drowning, cardiac by-pass surgery and cardiac arrest.

As described in greater detail in Example 1, a number of genes that are induced in the hippocampus by such protective hypoxic-ischemic treatment have been identified using rat model systems. These genes were identified by performing differential cloning between preconditioned and normal rat brains and sequencing the differentially expressed genes. This sequence information was subsequently utilized to conduct sequence comparisons with sequences available in public databases using standard sequence algorithms (e.g., BLAST). Of the differentially expressed genes identified, four independent clones were identified that match the sequence for rat UCP-2 (Genbank ID: AB010743). UCP-2 upregulation in an ischemic preconditioning model in which preconditioning confers a protective effect against subsequent neurological insults indicates that an increase in UCP-2 activity can have a neuroprotective effect on various neurological cell types (e.g., neurons, glial cells, microglial cells), thereby protecting against various neurological disorders, including but not limited to, stroke and ischemic stroke. Thus, agents able to increase the expression levels or activity of UCP-2 can potentially have a neuroprotective effect.

The role that UCP-2 plays in regulating mitochondrial membrane potential also indicates that agents that alter mitochondrial permeability are also candidates for providing a neuroprotective effect. As described more fully in the Examples below, the evidence indicates that the mechanism of action for UCP-2 involves inhibition of cell apoptosis, which in turn is a consequence of a cascade of events involving the mitochondrial permeability transition.

Apoptosis, or programmed cell death, plays a fundamental role in normal biological processes as well as in several disease states (see, e.g., Nicholson and Thornberry, (1996) Trends Biochem. Sci. 22:299–306; and Thompson (1995) Science 281:1312–1316). Apoptosis can be induced by various stimuli that all produce the same end result: systematic and deliberate cell death. One apoptotic cascade is triggered by mitochondrial permeability transition which consists in the opening of a voltage-sensitive pore that allows solutes to equilibrate across the mitochondrial membrane. Mitochondria participate in apoptotic signaling by mediating the activation of caspases via release of cytochrome c to the cytosol. Thus, localization of cytochrome c serves as a convenient marker for studying mitochondrial involvement in apoptosis. Caspases are cysteine proteases that possess the unusual ability to cleave substrates after aspartate residues; this activity is central to their role in apoptosis. Upon activation, caspases disable cellular homeostatic and repair processes, and cleave important structural components in the cell. Caspase-3 plays a direct role in proteolytic digestion of cellular proteins responsible for progression to apoptosis (see, e.g., Fernandes-Alnemri et al. (1994) J. Biol. Chem. 269:30761–30764).

The mechanisms underlying the neuroprotective role of UCP-2 may include inhibition and/or regulation of any of the components of the apoptotic cascade including, but not limited to, effects on mitochondrial membrane potential and mitochondrial permeability transition, blockade of cytochrome c release from mitochondria, and activation of caspases, as evidenced in the Examples below. That UCP-2 is a mitochondrial protein capable of lowering the mitochondrial matrix pH, reducing free-radical levels and ATP production, which are involved in neuronal apoptosis, is consistent with such a mechanism.

The finding of UCP-2 upregulation as a mechanism for providing a protective neurological effect and the evidence indicating its role in inhibiting apoptosis provides the basis for a number of diagnostic and therapeutic methods, as well as screening methods. Agents that influence UCP-2 activity or expression can potentially provide a more effective neuroprotective effect than agents that interact with a downstream component of an apoptotic cascade (e.g., caspase 3). Because UCP-2 occurs early in the apoptotic cascade, it has the potential to affect a greater number of cellular pathways than a component that is further downstream in the cascade. These various diagnostic, treatment and screening methods are discussed further below.

IV. Diagnostic and Prognostic Methods

The differential expression of UCP-2 in response to an ischemic event indicates that UCP-2 can serve as a marker for diagnosing individuals that have suffered a mild stroke, and in prognostic evaluations to detect individuals at risk for stroke. Prognostic methods can also be utilized in the assessment of the severity of the stroke and the likelihood of recovery.

In general, such diagnostic and prognostic methods involve detecting an elevated level of UCP-2 in the cells or tissue of an individual or a sample therefrom. A variety of different assays can be utilized to detect an increase in UCP-2 expression, including both methods that detect UCP-2 transcript and UCP-2 protein levels. More specifically, the diagnostic and prognostic methods disclosed herein involve obtaining a sample from an individual and determining at least qualitatively, and preferably quantitatively, the level of UCP-2 expression in the sample. Usually this determined value or test value is compared against some type of reference or baseline value. Details regarding samples, methods for quantitating expression levels and controls are set forth in the following sections.

A. Detection of Transcript

A number of different methods for detecting and optionally quantitating UCP-2 transcript are available and known to those of skill in the art. Examples of suitable methods for detecting an quantifying changes in UCP-2 expression include, but are not limited to, dot blots, in-situ hybridization, nucleic acid probe arrays, quantitative reverse-transcription PCR, (RT-PCR), Northern blots and RNAase protection methods.

1. Dot Blots and In-situ Hybridization

Dot blots are one example of an assay that can be utilized to determine the amount of UCP-2 transcript present in a nucleic acid sample obtained from an individual being tested. In these assays, a sample from an individual being tested for stroke is spotted on a support (e.g., a filter) and then probed with labeled nucleic acid probes that specifically hybridize with UCP-2 nucleic acids. After the probes have been allowed to hybridize to the immobilized nucleic acids on the filter, unbound nucleic acids are rinsed away and the presence of hybridization complexes detected and quantitated on the basis of the amount of labeled probe bound to the filter.

In-situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes for UCP-2 is then contacted with the cells and the probes allowed to hybridize with UCP-2 nucleic acids. Excess probe is digested, washed away and the amount of hybridized probe measured. This approach is described in greater detail by Harris, D. W. (1996) Anal. Biochem. 243:249–256; Singer, et al. (1986) Biotechniques 4:230–250; Haase et al. (1984) Methods in Virology, vol. VII, pp. 189–226; and Nucleic Acid Hybridization: A Practical Approach (Hames, et al., eds., 1987).

The hybridization probes utilized in the foregoing methods are polynucleotides that are of sufficient length to specifically hybridize to a UCP-2 nucleic acid. Hybridization probes are typically at least 15 nucleotides in length, in some instances 20 to 30 nucleotides in length, in other instances 30 to 50 nucleotides in length, and in still other instances up to the full length of a UCP-2 nucleic acid. The probes are labeled with a detectable label, such as a radiolabel, fluorophore, chromophore or enzyme to facilitate detection. Methods for synthesizing the necessary probes include the phosphotriester method described by Narang et al. (1979) Methods of Enzymology 68:90, and the phosphodiester method disclosed by Brown et al. (1979) Methods of Enzymology 68:109.

2. Nucleic Acid Probe Arrays

Related hybridization methods utilize nucleic acid probe arrays to detect and quantitate UCP-2 transcript. The arrays utilized to detect UCP-2 can be of varying types. The probes utilized in the arrays can be of varying types and can include, for example, synthesized probes of relatively short length (e.g., a 20-mer or a 25-mer), cDNA (full length or fragments of gene), amplified DNA, fragments of DNA (generated by restriction enzymes, for example) and reverse transcribed DNA (see, e.g., Southern et al. (1999) Nature Genetics Supplement 21:5–9 (1999). Both custom and generic arrays can be utilized in detecting UCP-2 expression levels. Custom arrays can be prepared using probes that hybridize to particular preselected subsequences of mRNA gene sequences of UCP-2 or amplification products prepared from them. Generic arrays are not specially prepared to bind to UCP-2 sequences but instead are designed to analyze mRNAs irrespective of sequence. Nonetheless, such arrays can still be utilized because UCP-2 nucleic acids only hybridize to those locations that include complementary probes. Thus, UCP-2 levels can still be determined based upon the extent of binding at those locations bearing probes of complementary sequence.

In probe array methods, once nucleic acids have been obtained from a test sample, they typically are reversed transcribed into labeled cDNA, although labeled mRNA can be used directly. The test sample containing the labeled nucleic acids is then contacted with the probes of the array. After allowing a period sufficient for any labeled UCP-2 nucleic acid present in the sample to hybridize to the probes, the array is typically subjected to one or more high stringency washes to remove unbound nucleic acids and to minimize nonspecific binding to the nucleic acid probes of the arrays. Binding of labeled UCP-2 is detected using any of a variety of commercially available scanners and accompanying software programs.

For example, if the nucleic acids from the sample are labeled with fluorescent labels, hybridization intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stem et al. and are available from Affymetrix, Inc., under the GeneChip™ label. Some types of label provide a signal that can be amplified by enzymatic methods (see Broude, et al., *Proc. Natl. Acad. Sci. U.S.A.* 91, 3072–3076 (1994)). A variety of other labels are also suitable including, for example, radioisotopes, chromophores, magnetic particles and electron dense particles.

Those locations on the probe array that are hybridized to labeled nucleic acid are detected using a reader, such as described by U.S. Pat. No. 5,143,854, WO 90/15070, and U.S. Pat. No. 5,578,832. For customized arrays, the hybridization pattern can then be analyzed to determine the presence and/or relative amounts or absolute amounts of known mRNA species in samples being analyzed as described in e.g., WO 97/10365.

Further guidance regarding the use of probe arrays sufficient to guide one of skill in the art is provided in WO 97/10365, PCT/US/96/143839 and WO 97/27317. Additional discussion regarding the use of microarrays in expression analysis can be found, for example, in Duggan, et al., Nature Genetics Supplement 21:10–14 (1999); Bowtell, Nature Genetics Supplement 21:25–32 (1999); Brown and Botstein, Nature Genetics Supplement 21:33–37 (1999); Cole et al., Nature Genetics Supplement 21:38–41 (1999); Debouck and Goodfellow, Nature Genetics Supplement 21:48–50 (1999); Bassett, Jr., et al., Nature Genetics Supplement 21:51–55 (1999); and Chakravarti, Nature Genetics Supplement 21:56–60 (1999).

3. Quantitative RT-PCR

A variety of so-called "real time amplification" methods or "real time quantitative PCR" methods can also be utilized to determine the quantity of UCP-2 mRNA present in a sample. Such methods involve measuring the amount of amplification product formed during an amplification process. Fluorogenic nuclease assays are one specific example of a real time quantitation method that can be used to detect and quantitate UCP-2 transcript. In general such assays continuously measure PCR product accumulation using a dual-labeled fluorogenic oligonucleotide probe—an approach frequently referred to in the literature simply as the "TaqMan" method.

The probe used in such assays is typically a short (ca. 20–25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For measuring UCP-2 transcript, the probe is designed to have at least substantial sequence complementarity with a probe binding site on UCP-2 transcript. Upstream and downstream PCR primers that bind to regions that flank UCP-2 are also added to the reaction mixture for use in amplifying UCP-2.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter dye from the polynucleotide-quencher complex and resulting in an increase of reporter emission intensity that can be measured by an appropriate detection system.

One detector which is specifically adapted for measuring fluorescence emissions such as those created during a fluorogenic assay is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986–994 (1996); Gibson, U. E. M, et al., Genome Research 6:995–1001 (1996); Holland, P. M., et al., Proc. Natl. Acad. Sci. USA 88:7276–7280, (1991); and Livak, K. J., et al., PCR Methods and Applications 357–362 (1995), each of which is incorporated by reference in its entirety.

4. Northern Blots

Northern blots can be used to detect and quantitate UCP-2 transcript. Such methods typically involve initially isolating total cellular or poly(A) RNA and separating the RNA on an agarose gel by electrophoresis. The gel is then overlaid with a sheet of nitrocellulose, activated cellulose, or glass or nylon membranes and the separated RNA transferred to the sheet or membrane by passing buffer through the gel and onto the sheet or membrane. The presence and amount of UCP-2 transcript present on the sheet or membrane can then be determined by probing with a labeled probe complementary to UCP-2 to form labeled hybridization complexes that can be detected and optionally quantitated (see, e.g., . Sambrook, et al. (1989) Molecular Cloning—A Laboratory Manual (2nd ed) Vols. 1–3, Cold Spring Harbor Laboratory, Cold Spring Harbor Press, NY).

5. RNAase Protection Assays

Ribonuclease protection assays (RPA) involve preparing a labeled antisense RNA probe for UCP-2. This probe is subsequently allowed to hybridize in solution with UCP-2 transcript contained in a biological sample to form RNA:RNA hybrids. Unhybridized RNA is then removed by digestion with an RNAase, while the RNA:RNA hybrid is protected from degradation. The labeled RNA:RNA hybrid is separated by gel electrophoresis and the band corresponding to UCP-2 detected and quantitated. Usually the labeled RNA probe is radiolabeled and the UCP-2 band detected and quantitated by autoradiography. RPA is discussed further by (Lynn et al. (1983) Proc. Natl. Acad. Sci. 80:2656; Zinn, et al. (1983) Cell 34:865; and Sambrook, et al. (1989) Molecular Cloning—A Laboratory Manual (2nd ed) Vols. 1–3, Cold Spring Harbor Laboratory, Cold Spring Harbor Press, NY).

B. Detection of UCP-2 Translation Product

Instead of detecting an increase in transcript, another option for detecting UCP-2 expression is to determine UCP-2 protein levels and/or activity. A number of different approaches can be utilized to accomplish this, including the use of antibodies that specifically bind UCP-2 and assays that measure UCP-2 activity (e.g., mitochondrial respiration).

1. Immunological Methods

One method for determining the expression level of UCP-2 is to utilize antibodies that specifically bind to UCP-2 to capture UCP-2 from a sample. One such approach is the so-called "sandwich immunoassay." Such methods generally involve contacting a sample from an individual with immobilized anti-UCP-2 antibodies which capture UCP-2 from the sample to form a complex. This complex is subsequently contacted with a labeled anti-UCP-2 detection antibody that preferably recognizes a different portion of UCP-2 then the immobilized antibody. This detection antibody binds to the complex containing UCP-2 and immobilized antibody to form a ternary complex that can be quantitated based upon the magnitude of a signal generated by the labeled detection antibody. Certain of the sandwich assays are enzyme-linked immunosorbent assays (ELISA) in which the detection antibody bears an enzyme. The detection antibody is detected by providing a substrate for the enzyme to generate a detectable signal.

Further guidance regarding the methodology and steps of a variety of antibody assays is provided, for example, in U.S. Pat. No. 4,376,110 to Greene; "Immunometric Assays Using Monoclonal Antibodies," in *Antibodies: A Laboratory Manual*, Cold Spring Harbor Laboratory, Chap. 14 (1988); Bolton and Hunter, "Radioimmunoassay and Related Methods," in *Handbook of Experimental Immunology* (D. M. Weir, ed.), Vol. 1, chap. 26, Blackwell Scientific Publications, 1986; Nakamura, et al., "Enzyme Immunoassays: Heterogeneous and Homogenous Systems," in *Handbook of Experimental Immunology* (D. M. Weir, ed.), Vol. 1, chap. 27, Blackwell Scientific Publications, 1986; and Current Protocols in Immunology, (John E. Coligan, et al., eds), chap. 2, section I, (1991).

The antibodies used to perform the foregoing assays can include polyclonal antibodies, monoclonal antibodies and fragments thereof as described supra. Monoclonal antibodies can be prepared according to established methods (see, e.g., Kohler and Milstein (1975) Nature 256:495; and Harlow and Lane (1988) Antibodies: A Laboratory Manual (C.H.S.P., N.Y.)).

2. Activity Assays

Various different UCP-2 activities can also be determined to detect an increase in UCP-2 expression. For example, given its uncoupling role in mitochondria, certain assays involve detecting an increase in mitochondrial respiration mediated by UCP-2 in a sample from a patient potentially suffering from stroke or at risk for stroke relative to a baseline value. Assays can be conducted using isolated cells or tissue samples, or isolated mitochondrial preparations. Instead of measuring mitochondrial respiration, one can instead measure the extent of mitochondrial swelling. Methods for conducting such mitochondrial assays are known in the art and described, for example, by Salvioli et al. (1997) FEBS Lett 411:77–82; and Smiley et al. (1991) Proc. Natl. Acad. Sci. USA 88:3671–3675). Methods for conducting such assays with certain uncoupling proteins is discussed, for example, in PCT publications WO 00/17353 and WO 98/45313.

By analogy to UCP-1 activity, another activity that can serve as a measure of UCP-2 activity in some instances is the transport of fatty acids by UCP-2. UCP-1 proton transport activity is regulated by fatty acids. In vitro studies also show that UCP-1 can function as a fatty acid anion transporter. It is believed that fatty acids stimulate proton transport across the mitochondrial membrane by themselves mediating the transport of protons as UCP-1 protonophores (see, e.g., Garlid, K. D., et al. (1996) J. Biol. Chem. 271:2615–2620). The sequence homology between UCP-1 and UCP-2 indicates that UCP-2 activity also includes fatty acid transport. Such assays can be conducted using labeled (e.g., radiolabeled) fatty acids.

C. Time Course Analyses

Certain prognostic methods of assessing a patient's risk of stroke involve monitoring UCP-2 expression levels for a patient susceptible to stroke to track whether there appears to be an increase in UCP-2 expression over time. An increase in UCP-2 expression over time can indicate that the individual is at increased risk for stroke. As with other measures of UCP-2, the UCP-2 expression level for the patient at risk for stroke is compared against a baseline value (see infra). The baseline in such analyses can be a prior value determined for the same individual or a statistical value (e.g., mean or average) determined for a control group (e.g., a population of individuals with no apparent neurological risk factors). An individual showing a statistically significant increase in UCP-2 expression levels over time can prompt the individual's physician to take prophylactic measures to lessen the individual's potential for stroke. For example, the physician can recommend certain life style changes (e.g., improved diet, exercise program) to reduce the risk of stroke. Alternatively, or in addition, the physician can prescribe medicines to reduce the stroke risk.

D. Controls

The various test values determined for a sample from an individual believed to have suffered a stroke or to be susceptible to stroke typically are compared against a baseline value to assess the extent of increased UCP-2 expression, if any. This baseline value can be any of a number of different values. In some instances, the baseline value is a value established in a trial using a healthy cell or tissue sample that is run in parallel with the test sample. Alternatively, the baseline value can be a statistical value (e.g., a mean or average) established from a population of control cells or individuals. For example, the baseline value can be a value or range which is characteristic of a control individual or control population. For instance, the baseline value can be a statistical value or range that is reflective of UCP-2 levels for the general population, or more specifically, healthy individuals not susceptible to stroke. Individuals not susceptible to stroke generally refer to those having no apparent risk factors correlated with stroke, such as high blood pressure, high cholesterol levels, diabetes, smoking and high salt diet, for example.

E. Samples

Samples can be obtained from a variety of sources. For example, since the methods are designed primarily to diagnosis and assess risk factors for humans to neurological disorders such as stroke, samples are typically obtained from a human subject. However, the methods can also be utilized with samples obtained from all other mammals, such as non-human primates (e.g., apes and chimpanzees), mice and rats. Such samples can be referred to as a patient sample or a biological sample.

Samples can be obtained from the tissues or fluids of an individual, as well as from cell cultures or tissue homogenates. For example, samples can be obtained from whole blood, serum, semen, saliva, tears, urine, fecal material, sweat, buccal, skin, spinal fluid and amniotic fluid. Samples can also be derived from in vitro cell cultures, including the growth medium, recombinant cells and cell components.

Because certain diagnostic methods involve evaluating the level of expression in nerve cells, the sample can be obtained from various types of nerve cells including, but not limited to, neuron cells, glial cells, microglial cells and cortical neuron cells. Current evidence indicates that one consequence of stroke is that the blood/brain barrier becomes more permeable. Stroke also results in the death of certain cells which, upon dying, are lysed, thus expelling cellular components such as UCP-2. These components can then traverse the blood/brain barrier and be picked up by the circulatory system. Consequently, certain diagnostic and prognostic methods are conducted with blood samples.

Because UCP-2 is expressed as part of a neuroprotective response, diagnostic samples are collected any time after an individual is suspected to have had a stroke or to exhibit symptoms that are predictors of stroke. In prophylactic testing, samples can be obtained from an individual who present with risk factors that indicate a susceptibility to stroke (e.g., high blood pressure, obesity, diabetes) as part of a routine assessment of the individual's health status.

Some of the diagnostic and prognostic methods that involve the detection of UCP-2 transcript begin with the lysis of cells and subsequent purification of nucleic acids from other cellular material. To measure the transcription level (and thereby the expression level) of UCP-2, a nucleic acid sample comprising mRNA transcript(s) of UCP-2, or nucleic acids derived from the mRNA transcript(s) is obtained. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include, but are not limited to, mRNA transcripts of UCP-2, cDNA reverse transcribed from the mRNA, cRNA transcribed from the cDNA, DNA amplified from UCP-2 nucleic acids, and RNA transcribed from amplified DNA.

In some methods, a nucleic acid sample is the total mRNA isolated from a biological sample; in other instances, the nucleic acid sample is the total RNA from a sample taken from an individual. Any RNA isolation technique such as those described supra that do not select against the isolation of mRNA can be utilized for the purification of such RNA samples. If needed to improve the detection limits of the method, UCP-2 can be amplified prior to further analysis using established amplification techniques such as those described above.

IV. Therapeutic/Prophylactic Treatment Methods

A. General

The upregulation of UCP-2 detected in the neuroprotection model system indicates that methods that increase the expression or activity of UCP-2 can be utilized in treating individuals that have suffered a neuronal injury, as well as prophylactically treating individuals at risk for neuronal injury. In general, such methods involve administering to an individual that has suffered a neurological injury or that is at risk for such injury, an agent in an amount effective to increase the expression or activity of UCP-2. The neurological injury being treated can include, stroke (particularly ischemic stroke), and all other neurological diseases associated with altered mitochondrial function including, but not limited to, Alzheimer's Disease, Parkinson's Disease, Huntington's Disease, inherited ataxias, schizophrenia, dementia, mitochondrial encephalopathy, amylotrophic lateral sclerosis, motor neuron diseases and others (see, e.g., Beal (2000) TINS 23: 298). In a broader view, mitochondrial dysfunction is a critical factor in cell death by necrosis and apoptosis. Thus, many diseases (neurological and peripheral) involving cell death by apoptosis and/or necrosis can be targeted by an increase in UCP-2 activity (e.g., myocardial ischemia, diabetes, hepatic cierrosis, muscular dystrophies, spinal cord injuries).

Therapeutic/prophylactic intervention to increase UCP-2 expression and/or activity include but are not limited to administration of UCP-2 inducers shortly after an ischemic episode, and chronic administration in individuals with a previous stroke, at higher risk for stroke, and in genetically predisposed individuals.

Depending upon the individual's condition, the agent can be administered in a therapeutic or prophylactic amount. If the individual has suffered a neurological injury, then, at least for some period of time after the injury, the agent is typically administered in a therapeutic amount. A "therapeutic amount," as defined herein, means an amount sufficient to remedy a neurological disease state or symptoms, or otherwise prevent, hinder, retard or reverse the progression of a neurological disease or any other undesirable symptoms, especially stroke and more particularly ischemic stroke. If, however, the individual only presents with risk factors suggesting he or she is susceptible to neurological injury, then the agent is administered in a prophylactically effective amount. A prophylactic amount can also be administered as part of a long-term regimen for individuals that have already had a stroke and are at increased risk of another stroke. A "prophylactic amount" is an amount sufficient to prevent, hinder or retard a neurological disease or any undesirable symptom, particularly with regard to neurological disorders such as stroke, particularly ischemic stroke.

Prophylactic treatment can commence whenever an individual is at increased risk of suffering from a neurological disorder such as stroke. For example, individuals having risk factors known to be correlated with stroke can be administered prophylactic amounts of an agent that increases UCP-2 activity. Examples of such individuals include those that: are overweight or obese, have high blood pressure, have elevated cholesterol levels, have diabetes and/or are about to undergo medial treatment that puts the individual at risk (e.g., a patient about to undergo cardiac by-pass surgery).

In view of UCP-2 activity as a mitochondrial protein that regulates mitochondrial permeability transition, agents utilized in therapeutic methods can include those that affect the mitochondrial transition pore in a similar manner. Similarly, given the evidence indicating that UCP-2 inhibits apoptosis at least in part by inhibiting caspase 3 activation, therapeutic agents can also include agents with similar inhibitory properties.

B. UCP-2 and Other Agents

A variety of different agents can be administered to achieve the desired increase in UCP-2 activity. In some instances, the agent is a purified UCP-2 polypeptide as defined supra, including active fragments thereof. Methods for preparing purified UCP-2 are described infra. Other therapeutic agents that are administered act to stimulate the synthesis or expression of UCP-2. Such agents include those that induce the UCP-2 promoter, for example, thereby increasing expression of UCP-2 in cells. Compounds having such activity can be identified using the screening methods described below in the screening section. Often such compounds are administered in combination with a pharmaceutically-acceptable carrier. Such carriers and modes of administration are discussed further in the section on pharmaceutical compositions infra. Various inducers of UCP-2 can be utilized in certain methods. Specific examples of such inducers include PPARγ agonists such as β3-agonists such as isoproterenol. Inducers can also include agents that activate the transcription of UCP-2.

Compounds increasing UCP-2 activity can be administered in combination with various other compounds. For example, the compound can be administered with an agent that increases the permeability of the blood/brain barrier to facilitate delivery of the agent activating UCP-2 activity to the brain. Such agents include, but are not limited to, bradykinin, serotonin, histamine and arachidonic acid. Other compounds that can be administered with the compound increasing UCP-2 activity include compounds that protect against clotting and prevent thrombus formation including but not limited to heparin and fucoidan.

Because UCP-2 is transmembrane protein of the inner mitochondrial membrane that functions as a proton channel (Ricquier and Bouillaud (2000) Biochem J 345: 161–179), identification of agonists that increase UCP-2 activity are another therapeutic option (see, generally, Drews (2000) Science 287: 1960 for a discussion of drug targets to ion channels). These agonists can gate the UCP-2 channel in the absence of physiological regulation and gating mechanisms and lead to an increase in UCP-2-mediated proton flow.

Additional agents that can be administered in combination with the identified compounds and delivery mode options are discussed in detail in the pharmaceutical composition section infra.

C. Gene Therapy

Gene therapy is another option for increasing UCP-2 expression. Such methods generally involve administering to an individual a nucleic acid molecule that encodes UCP-2 or an active fragment thereof. The administered nucleic acid increases the level of UCP-2 expression in one or more tissues, especially nerve cells, and particularly neuron cells. The nucleic acid is administered to achieve synthesis of UCP-2 in an amount effective to obtain a therapeutic or prophylactic effect in the individual receiving the therapy. As used herein, the term "gene therapy" refers to therapies in which a lasting effect is obtained with a single treatment, and methods wherein the gene therapeutic agents are administered multiple times to achieve or maintain the desired increase in UCP-2 expression.

The nucleic acid molecules encoding UCP-2 can be administered ex vivo or in vivo. Ex vivo gene therapy methods involve administering the nucleic acid to cells in vitro and then transplanting the cells containing the introduced nucleic acid back into the individual being treated. Techniques suitable for the in vitro transfer of UCP-2 nucleic acids into mammalian cells include, but are not limited to, the use of liposomes, electroporation, microinjection, cell fusion, DEAE-dextran and calcium phosphate precipitation methods. Once the cells have been transfected, they are subsequently introduced into the patient.

Certain ex vivo methods are based on the use of any form of genetically-modified neuronal stem cells for the continuous intracerebral delivery of UCP-2. For example, UCP-2 producing cells can be implanted or surrounded by a semipermeable membrane (e.g., a capsule), directly into the intracerebroventricular space or into the cerebrospinal fluid.

In vivo gene therapy methods involve the direct administration of nucleic acid or a nucleic acid/protein complex into the individual being treated. In vivo administration can be accomplished according to a number of established techniques including, but not limited to, injection of naked nucleic acid, viral infection, transport via liposomes and transport by endocytosis. Of these, transfection with viral vectors and viral coat protein-liposome mediated transfection are commonly used methods (see, e.g., Dzau et al (1993) Trends in Biotechnology 11:205–210). Suitable viral vectors include, for example, adenovirus, adeno-associated virus and retrovirus vectors.

Methods can be designed to selectively deliver nucleic acids to certain cells. Examples of such cells include, neurons, astrocytes, oligodendrocytes, microglia, and endothelial cells. Because UCP-2 exhibits a neuroprotective effect, certain treatment methods are designed to selectively express UCP-2 in neuron cells and/or target the nucleic acid for delivery to nerve cells. However, in other instances non-nerve cells are targeted (see, e.g., microglia, astrocytes, endothelial cells, oligodendrocytes). One technique for achieving selective expression in nerve cells is to operably link the nucleic acid encoding UCP-2 to a promoter that is primarily active in nerve cells. Examples of such promoters include, but are not limited to, prion protein promoter, calcium-calmodulin dependent protein kinase promoter, enolase promoter and PDGFβ-promoter. Alternatively, or in addition, the nucleic acid can be administered with an agent that targets the nucleic acid to nerve cells. For instance, the nucleic acid can be administered with an antibody that specifically binds to a cell-surface antigen on the nerve cells or a ligand for a receptor on neuronal cells. When liposomes are utilized, substrates that bind to a cell-surface membrane protein associated with endocytosis can be attached to the liposome to target the liposome to nerve cells and to facilitate uptake. Examples of proteins that can be attached include capsid proteins or fragments thereof that bind to nerve cells, antibodies that specifically bind to cell-surface proteins on nerve cells that undergo internalization in cycling and proteins that target intracellular localizations within nerve cells (see, e.g., Wu et al. (1987) J. Biol. Chem. 262:4429–4432; and Wagner, et al. (1990) Proc. Natl. Acad. Sci. USA 87:3410–3414). Gene marking and gene therapy protocols are reviewed by Anderson et al. (1992) Science 256:808–813.

Various other delivery options can also be utilized. For instance, a nucleic acid containing UCP-2 (e.g., a vector containing UCP-2) can be injected directly into the cerebrospinal fluid. Alternatively, such nucleic acids can be administered by intraventricular injections.

V. Screening Methods

A number of different screening protocols can be utilized to identify agents that increase the level of expression of UCP-2 in cells, particularly mammalian cells, especially human cells. In general terms, the screening methods involve screening a plurality of agents to identify an agent that increases the activity of UCP-2 by binding to UCP-2, preventing an inhibitor from binding to UCP-2 or activating expression of UCP-2, for example.

A. UCP-2 Binding Assays

Preliminary screens can be conducted by screening for compounds capable of binding to UCP-2, as at least some of the compounds so identified are likely UCP-2 activators. The binding assays usually involve contacting a UCP-2 protein with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61–89. The UCP-2 protein utilized in such assays can be naturally expressed, cloned or synthesized UCP-2.

B. Expression Assays

Certain screening methods involve screening for a compound that up-regulates the expression of UCP-2. Such methods generally involve conducting cell-based assays in which test compounds are contacted with one or more cells expressing UCP-2 and then detecting and an increase in UCP-2 expression (either transcript or translation product). Some assays are performed with neuron cells that express endogenous UCP-2 (e.g., cortical neuron cells, glial cells or microglial cells). Other expression assays are conducted with non-neuronal cells that express an exogenous UCP-2.

UCP-2 expression can be detected in a number of different ways. As described infra, the expression level of UCP-2 in a cell can be determined by probing the mRNA expressed in a cell with a probe that specifically hybridizes with a transcript (or complementary nucleic acid derived therefrom) of UCP-2. Probing can be conducted by lysing the cells and conducting Northern blots or without lysing the cells using in situ-hybridization techniques (see above). Alternatively, UCP-2 protein can be detected using immunological methods in which a cell lysate is probe with antibodies that specifically bind to UCP-2.

Other cell-based assays are reporter assays conducted with cells that do not express UCP-2. Certain of these assays are conducted with a heterologous nucleic acid construct that includes a UCP-2 promoter that is operably linked to a reporter gene that encodes a detectable product. Suitable UCP-2 promoters are described, for example, in PCT Publication WO 00039315. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) Nature 282:864–869), luciferase, β-galactosidase and alkaline phosphatase (Toh, et al. (1980) Eur. J. Biochem. 182:231–238; and Hall et al. (1983) J. Mol. Appl. Gen. 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression of UCP-2 and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of UCP-2 expression levels for a control population (e.g., healthy individuals not at risk for neurological injury such as stroke). Expression levels can also be determined for cells that do not express UCP-2 as a negative control. Such cells generally are otherwise substantially genetically the same as the test cells.

A variety of different types of cells can be utilized in the reporter assays. As stated above, certain cells are nerve cells that express an endogenous UCP-2. Cells not expressing UCP-2 can be prokaryotic, but preferably are eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

C. Assays of UCP-2 Activity

Various screening methods can be conducted to identify compounds that increase the activity of UCP-2. Some of the UCP-2 activities that can be measured include determination of mitochondrial respiration and fatty acid transport rates as described supra in the section on diagnostic methods. The sequence homology between UCP-2 and UCP-1 indicates that under some conditions UCP-2 proton transport can be inhibited by certain purine nucleotides, such as diphosphate and triphosphate purine nucleotides. GDP, for instance, has be shown to be an inhibitor that binds to an inhibitory site on UCP-1 (see, e.g., Murdza-Inglis, D. L., et al. (1994) J. Biol. Chem. 269:7435–38; and Bouillaud, F., et al. (1994) EMBO J. 13:1990–97). Thus, screens to identify compounds that inhibit binding of such purine nucleotides either by binding to the same inhibitory site or at another site of UCP-2 can serve as potential activators of UCP-2. These type of compounds can be identified by using labeled-purine nucleotides, for example, and detecting the ability of test compounds to inhibit binding of the labeled nucleotides to UCP-2 (e.g., UCP-2 containing mitochondrial membrane preparations). Assays based on measuring the mitochondrial membrane potential, and the associated protonmotive force (PMF), can be performed in both yeast and mammalian cells upon ectopic expression of UCP-2. Compounds that influence the PMF can be subsequently identified by fluorescent dyes or electrochemical methods.

Other assays can also be utilized in the screening process. Examples include assaying mitochondrial respiration rates, mitochondrial swelling and/or transport of fatty acids as described supra in the section diagnostic and prognostic methods. Regardless of the particular assay, various controls can be conducted to ensure that the observed activity is genuine. For example, assays can be conducted with cells that do not express UCP-2 or assays can be conducted in which cells that do express UCP-2 are not contacted with test compound.

D. Validation

Compounds that are initially identified by any of the foregoing screening methods can be further tested to validate the apparent activity. Preferably such studies are conducted with suitable animal models such as the rat model system described infra in Example 1. The basic format of such methods involves administering a lead compound identified during an initial screen to an animal that serves as a model for humans and then determining if UCP-2 is in fact upregulated. The animal models utilized in validation studies generally are mammals of any kind. Specific examples of suitable animals include, but are not limited to, primates, mice and rats.

Certain methods are designed to test not only the ability of a lead compound to increase UCP-2 activity in an animal model, but to provide protection after the animal has undergone transient ischemia for a longer period of time than shown to provide a protective effect. In such methods, a lead compound is administered to the model animal (i.e., an animal, typically a mammal, other than a human). The animal is subsequently subjected to transient ischemia for a period longer in duration than that shown to provide a protective effect. The conditions causing the ischemia are halted and UCP-2 activity monitored to identify those compounds still able to increase UCP-2 activity above a baseline level. Compounds able to enhance UCP-2 expression beyond the time period in which UCP-2 is upregulated in preconditioning models are good candidates for further study.

E. Compounds Affecting Mitochondria and Cell Apoptosis

Because of the evidence indicating that UCP-2 affects cellular apoptosis by altering mitochondrial permeability transition and membrane potential, as well as inhibiting activation of caspase-3 activation, screens can also be conducted to identify compounds that have similar effects on mitochondrial permeability transition, membrane potential and caspase-3 activation.

A variety of methods can be utilized to determine mitochondrial membrane potentials. One approach is to utilize fluorescent indicators(see, e.g., Haugland, 1996 Handbook of Fluorescent Probes and Research Chemicals, 6th ed., Molecular Probes, OR, pp. 266–274 and 589–594). Various non-fluorescent probes can also be utilized (see, e.g., Kamo et al. (1979) J. Membrane Biol. 49:105). Mitochondrial membrane potentials can also be determined indirectly from mitochondrial membrane permeability (see, e.g., Quinn (1976) The Molecular Biology of Cell Membranes, University Park Press, Baltimore, Md., pp. 200–217). Various ion sensitive electrode can also be utilized.

Caspase 3 activity can be monitored utilizing various known substrates known in the art. Suitable caspase-3 assays are described, for example, by (Ellerby et al., (1997) J. Neurosci. 17:6165; Rosen et al., (1997) J. Cell. Biochem. 64:50; and Kluck et al. (1997) Science 275:1132). Another caspase assay is described in Example 4 below.

Cytochrome c release from mitochondria can be detected using any of a number of immunological or spectroscopic methods.

F. Test Compounds

The screening methods can be conducted with essentially any type of compound potentially capable of activating UCP-2 expression. Consequently, test compounds can be of a variety of general types including, but not limited to, polypeptides; carbohydrates such as oligosaccharides and polysaccharides; polynucleotides; lipids or phospholipids; fatty acids; steroids; or amino acid analogs. The test compounds can be of a variety of chemical types including, but not limited to, heterocyclic compounds, carbocyclic compounds, β-lactams, polycarbamates, oligomeric-N-substituted glycines, benzodiazepines, thiazolidinones and imidizolidinones. Certain test agents are small molecules, including synthesized organic compounds.

Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

VI. Production of UCP-2

A. UCP-2 Nucleic Acids

UCP-2 nucleic acids can be obtained by any suitable method known in the art, including, for example: (1) hybridization of genomic or cDNA libraries with probes to detect homologous nucleotide sequences, (2) antibody screening of expression libraries to detect cloned DNA fragments with shared structural features, (3) various amplification procedures [e.g., polymerase chain reaction (PCR)] using primers that specifically hybridize to UCP-2 nucleic acids; and 4) direct chemical synthesis.

More specifically, UCP-2 nucleic acids can be obtained using established cloning methods. The nucleotide sequence of a gene or cDNA encoding UCP-2 (see, e.g., SEQ ID NO:1) is used to provide probes that specifically hybridize to a UCP-2 cDNA in a cDNA library, a UCP-2 gene in a genomic DNA sample, or to a UCP-2 mRNA in a total RNA sample (e.g., in a Southern or Northern blot). The libraries are preferably prepared from nerve cells. Once the target nucleic acid is identified, it can be isolated and cloned using well-known amplification techniques. Such techniques include, the polymerase chain reaction (PCR) the ligase chain reaction (LCR), Qβ-replicase amplification, the self-sustained sequence replication system (SSR) and the transcription based amplification system (TAS). Cloning methods that can be utilized to clone UCP-2 are described in Berger and Kimmel, Guide to Molecular Cloning Techniques, Methods in Enzymology, 152, Academic Press, Inc. San Diego, Calif.; Sambrook, et al. (1989) Molecular Cloning—A Laboratory Manual (2nd ed) Vols. 1–3, Cold Spring Harbor Laboratory, Cold Spring Harbor Press, NY; and Current Protocols (1994), a joint venture between Greene Publishing Associates, Inc. and John Wiley and Sons, Inc.

UCP-2 nucleic acids can also be obtained utilizing various amplification techniques. Such methods include, those described, for example, in U.S. Pat. No. 4,683,202 to Mullis et al.; PCR Protocols A Guide to Methods and Applications (Innis et al. eds) Academic Press Inc. San Diego, Calif. (1990); Kwoh et al. (1989) Proc. Natl. Acad. Sci. USA 86: 1173; Guatelli et al. (1990) Proc. Natl. Acad. Sci. USA 87: 1874; Lomell et al. (1989) J. Clin. Chem. 35: 1826; Landegren et al. (1988) Science 241: 1077–1080; Van Brunt (1990) Biotechnology 8: 291–294; Wu and Wallace (1989) Gene 4: 560; and Barringer et al. (1990) Gene 89: 117.

As an alternative to cloning a nucleic acid, a suitable nucleic acid can be chemically synthesized. Direct chemical synthesis methods include, for example, the phosphotriester method of Narang et al. (1979) Meth. Enzymol. 68: 90–99; the phosphodiester method of Brown et al. (1979) Meth. Enzymol. 68: 109–151; the diethylphosphoramidite method of Beaucage et al. (1981) Tetra. Lett., 22: 1859–1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes. The fragments can then be ligated to produce a UCP-2 sequence.

Further specific guidance regarding the preparation of UCP-2 nucleic acids is provided by Fleury et al. (1997) Nature Genetics 15:269–272; Tartaglia et al., PCT Publication No. WO 96/05861; and Chen, et al., PCT Publication No. WO 00/06087, each of which is incorporated herein in its entirety.

B. UCP-2 Proteins

UCP-2 proteins can be produced through isolation from natural sources, recombinant methods and chemical synthesis. For example, UCP-2 proteins can be prepared by expressing cloned UCP-2 in a host cell. Cloned UCP-2 sequences are expressed in hosts after the sequences have been operably linked to an expression control sequence in an expression vector. Expression vectors are usually replicable in the host organisms either as episomes or as an integral part of the host chromosomal DNA.

Typically, the polynucleotide that encodes UCP-2 is placed under the control of a promoter that is functional in the desired host cell to produce relatively large quantities of UCP-2. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, *E. coli*, other bacterial hosts, yeast, and various higher eukaryotic cells such as the COS, CHO and HeLa cells lines and myeloma cell lines.

Construction of suitable vectors containing one or more of the above listed components employs standard ligation techniques. A description of the preparation of the recombinant nucleic acids including sequences that encode UCP-2 can be found, for example, in Berger and Kimmel, Guide to Molecular Cloning Techniques, Methods in Enzymology, Volume 152, Academic Press, Inc., San Diego, Calif. (Berger); and Current Protocols in Molecular Biology, F. M. Ausubel et al., eds., Current Protocols, a joint venture between Greene Publishing Associates, Inc. and John Wiley & Sons, Inc., (1998 Supplement) (Ausubel).

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

As an option to recombinant methods, UCP-2 can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of UCP-2 can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993).

Additional guidance specific for preparing UCP-2 proteins is provided by Fleury et al. (1997) Nature Genetics 15:269–272; Tartaglia et al., PCT Publication No. WO 96/05861; and Chen, et al., PCT Publication No. WO 00/06087.

VII. Variations

A. Synthesis of Analogs

Active test agents identified by the screening methods described herein that increase UCP-2 activity can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Once analogs have been prepared, they can be screened using the methods disclosed herein to identify those analogs that exhibit an increased ability to increase UCP-2 activity. Such compounds can then be subjected to further analysis to identify those compounds that appear to have the greatest potential as pharmaceutical agents. Alternatively, analogs shown to have activity through the screening methods can serve as lead compounds in the preparation of still further analogs, which can be screened by the methods described herein. The cycle of screening, synthesizing analogs and rescreening can be repeated multiple times.

B. Pharmaceutical Compositions

1. Composition

Compounds identified by the screening methods described above, analogs thereof and UCP-2 itself can serve as the active ingredient in pharmaceutical compositions formulated for the treatment of various neurological disorders including stroke. The compositions can also include various other agents to enhance delivery and efficacy. For instance, compositions can include agents capable of increasing the permeability of the blood/brain barrier. Other agents that can be coadministered include anticoagulants and blood thinners. The compositions can also include various agents to enhance delivery and stability of the active ingredients.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide (e.g., UCP-2), the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527–1533 (1990).

2. Dosage

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

3. Administration

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules which consist of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The following examples are provided solely to illustrate in greater detail certain aspects of the invention and are not to be construed to limit the scope of the invention.

EXAMPLE 1

Differential Expression of UCP-2 in Preconditioning Rat Model

I. Background

Global cerebral ischemia of moderate duration causes selective neuronal degeneration in the hippocampus of rodent as well as human brains. Particularly sensitive are the pyramidal neurons in a sub-region of the hippocampus denoted CA1. This particular sensitivity to ischemia is an example of selective neuronal degeneration seen following global cerebral ischemia. The cell death process is a slowly evolving one that is not seen in the light microscope until 36–48 hrs of recovery following an ischemic insult of 10 minute duration. During this period, the neurons stay functional at least until 24 hours of recovery.

When a ten minute ischemic insult is preceded by a 3 minute ischemic insult in a defined time period, which by itself does not cause ischemic damage, no neuronal degeneration occurs in the CA1 region. This phenomenon is called ischemic preconditioning and is also seen in the heart and kidney, and possibly other organs.

II. Experimental/Results

A. Differential Expression of UCP-2

Rats of the same strain, age and sex were divided into two experimental groups: (a) animals in the first group, the "experimental group," underwent surgery including a single 3 minute bilateral occlusion of the carotid arteries to induce global ischemia under hypotension, and (b) animals in the second group were sham operated ("control group"). The sham operated animals were treated with cycloheximide and anesthetized, but not subjected to arterial occlusion. The animals were sacrificed 4 hours after the operation or being subjected to sham treatment and the CA1 region of their hippocampi were dissected. Poly-A+ RNA prepared from the collected tissues was converted into double-stranded cDNA (dscDNA). Subtractive hybridization was carried out using the dscDNA from preconditioned animals with an excess of dscDNA prepared from the sham operated animals. Differentially expressed gene fragments were cloned into a plasmid vector, and the resulting library was transformed in E. coli cells. Inserts of recombinant clones were amplified by the polymerase chain reaction (PCR). The PCR products (fragments of 200–2,000 bp in size) were sequenced using an oligonucleotide complementary to common vector sequences.

The differentially expressed fragments that were cloned included four independent clones: (a)SL3bE_F19 (SEQ ID NO:3); SL3bF_D20 (SEQ ID NO:4); SL3bC_M24 (SEQ ID NO:5); and SL3b_CP2_J11 (SEQ ID NO:6) whose expression level was found to be upregulated. The sequences determined for these clones were compared to public databases using the BLAST (blastn and tblastx) algorithm. The DNA sequence of these four clones was found to match the sequence for rat UCP-2 (Genbank ID:AB10743, *Rattus norvegicus* mRNA for UCP-2).

B. In situ Hybridization

A series of in situ hybridization experiments were conducted to confirm the CA1-specific upregulation of UCP-2 mRNA after ischemic preconditioning. In situ hybridization experiments were conducted on brain slices from the experimental and control rats using two different probes according to standard protocols [see, e.g., Harris, D. W. (1996) Anal. Biochem. 243:249–256; Singer, et al. (1986) Biotechniques 4:230–250; Haase et al. (1984) Methods in Virology, vol. VII, pp. 189–226; and Nucleic Acid Hybridization: A Practical Approach (Hames, et al., eds., 1987)]. The first probe, "oligo 28," had the sequence CTCTGGCAGGAACCCA-GAGAACCGTGGAGTCAAACAGAGCCAGG (SEQ ID NO:7). The second probe, oligo 33, had the sequence AGAAGTGAAGTGGCAAGGGAGGTCGTCT-GTCATGAGGTTGGCTT (SEQ ID NO:8).

Figure 2:
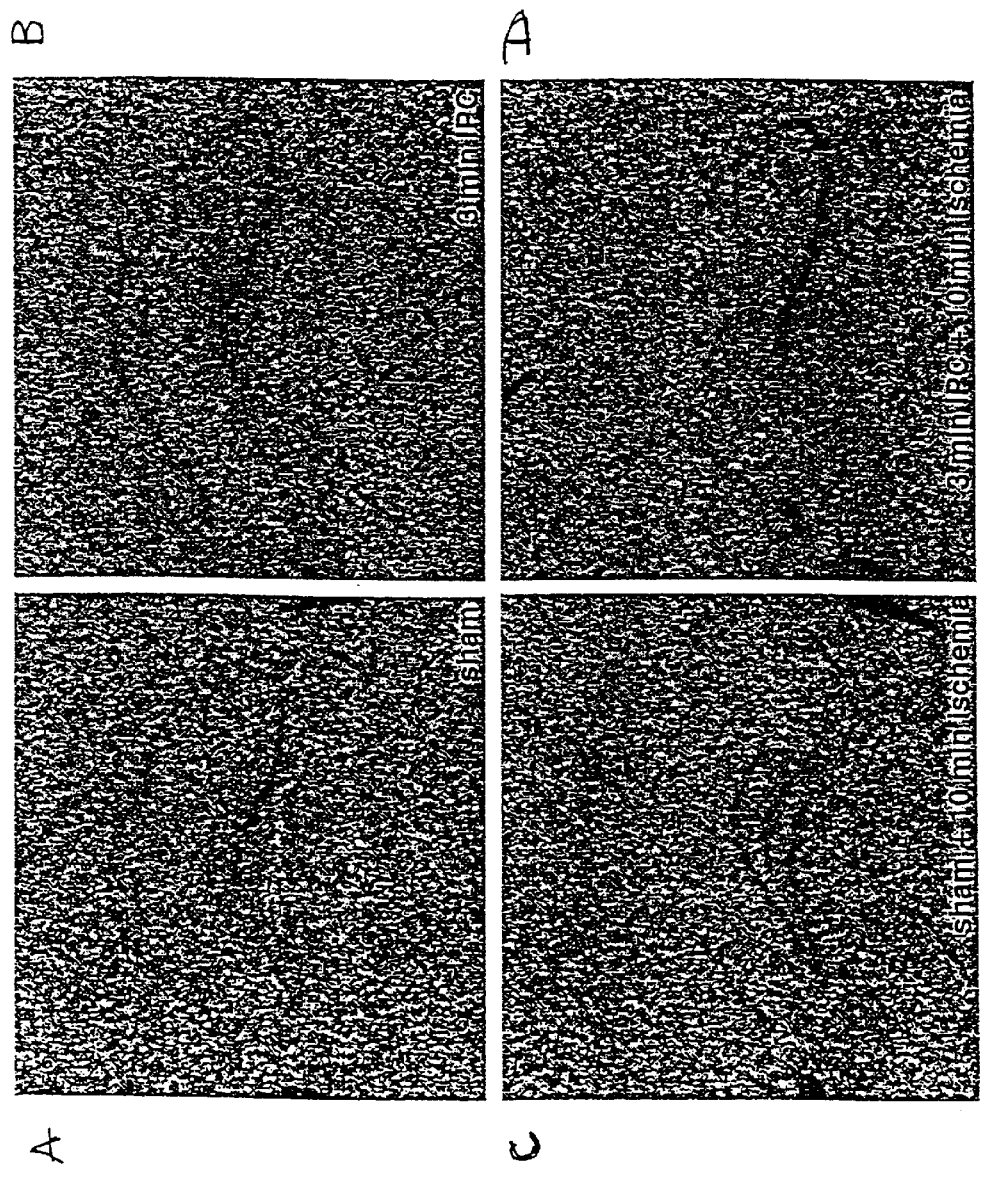
FIGS. 2A–2D are photomicrographs that illustrate the same events illustrated in FIGS. 1A–1D but utilizing a different labeled probe (oligo 33) that specifically hybridizes to UCP-2 mRNA.

The in-situ hybridization results are illustrated in FIGS. 1A–1D (results with oligo 28) and FIGS. 2A–2D (results with oligo 33). Using either oligo 28 or 33 as a probe, in rats under normal conditions UCP-2 mRNA expression is low in the CA1 region (sham; FIGS. 1A and 2A). This expression increases at 2 days following 3 minute ischemia (3 min IPC; FIGS. 1B and 2B). At one day after recovery following the 10 minute ischemia, i.e., approximately 12 hours prior to cell death, there is no increase in UCP-2 mRNA compared to controls (sh+10 min ischemia; FIGS. 1C and 2C). However, if the 10 minute ischemia period is preceded by a 3 minute episode of preconditioning, the expression of UCP-2 in the CA1 region increases (3 min IPC+10 min ischemia; FIGS. 1D and 2D). UCP-2 expression is highly expressed in the ischemia-resistant CA3 field of the rat hippocampus (FIGS. 1A–1D), as well as in the protected CA1 field after a combination of a 3 minute and 10 minute ischemic period (FIG. 1D). Thus, UCP-2 mRNA expression profile correlates well with the establishment of a neuroprotected state.

Utilizing in vivo and in vitro model systems of ischemic preconditioning, UCP-2 mRNA levels have been found to increase by approximately 1.5-fold in certain instances as measured using in-situ hybridization and cDNA. For quantification, in situ hybridization images were scanned and analyzed for pixel density in the CA1 field based on 5 independent in situ images. The pixel density in CA1 of sham (FIGS. 1A, 2A) was 23±10, the pixel density for the 3 min ischemia +48 h rec (FIGS. 1B, 2B) was 33±13. These results are statistically significant with a paired t-test value of p<0.011. As independent evidence, increase in UCP-2 mRNA expression levels have been also determined by cDNA arrays analysis: Recombinant inserts of the four UCP-2 containing clones (SL3bE_F19.Seq; SL3bF_D20.Seq; SL3bC_M24.Seq; and SL3b_CP2_J11.Seq) were arrayed on solid support and hybridized with labeled cDNA derived from CA1 regions of animals subjected to in vivo ischemic preconditioning and global ischemia, or with labeled cDNA derived from cortical neuronal cultures subjected to in vitro oxygen-glucose deprivation (see below). In both cases, compared to control CA1 regions or control cultures, a 1.5-fold increase in UCP-2 mRNA abundance was observed.

C. Western Blot Analysis of UCP-2 Expression

UCP-2 protein levels in rat preconditioned primary cortical neuronal cultures were analyzed with western blot. Primary cortical cell cultures were prepared from gestational day 17 fetal rats. Briefly, the cortex was dissected under a microscope, and the cells dissociated by trituration in modified Eagle's medium (MEM), 10% horse serum, 10% fetal bovine serum, 2 mM glutamine following a 30 min digestion in 0.027% trypsin/saline solution (Gibco BRL, Gaithersburg, Md.). Cells were plated in 15 mm multiwell (Nunc) plates coated with polyornithine at a density of 3–4×10$^5$ cells per well. Four days after plating, the cells were treated with 10 μg/ml of 5-fluoro-2'-deoxyuridine for 3 days to inhibit proliferation of non-neuronal cells. Cultures were maintained in MEM, 5% horse serum, 2 mM glutamine in 8% $CO_2$, humidified, 37° C. atmosphere. The medium was changed twice a week. Mature neurons (14 days in culture) were used for all experiments. Combined oxygen-glucose deprivation was performed by complete exchange of media with deoxygenated, glucose-free Earle's balanced salt solution (EBSS) containing 116 mM NaCl, 5.4 mM KCl, 0.8 mM $MgSO_4$, 1 mM $NaH_2PO_4$, and 0.9 mM $CaCl_2$, bubbled with 5% $H_2$/85% $N_2$/5% $CO_2$. The cultures were kept in an anaerobic chamber for 5 or 60 min containing the gas mixture. OGD was terminated by removal of the cultures from the chamber and replacement of the EBSS solution with oxygenated growth media.

Figure 3:
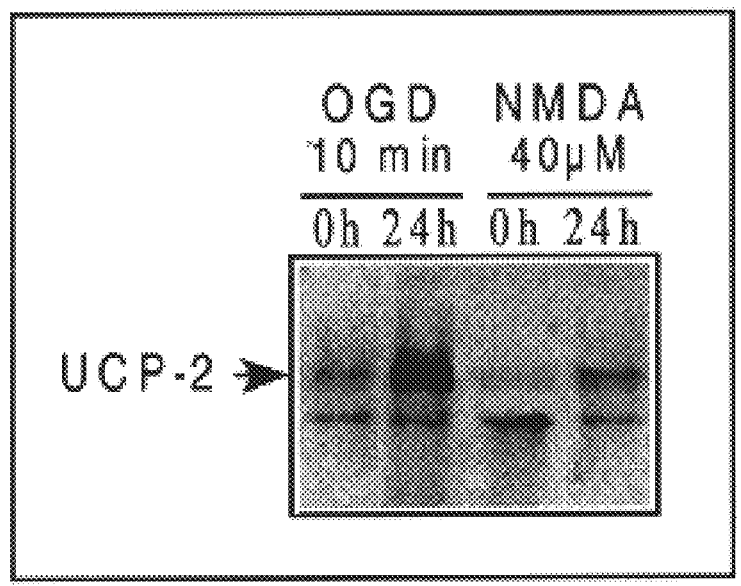
FIG. 3 shows western blot analysis of UCP-2 protein levels in rat primary cortical neuronal cultures preconditioned by exposure to OGD for 10 min or to 40 $\mu$M NMDA for 5 min.

Increased levels of UCP-2 protein were observed in the cortical neuronal cultures preconditioned by exposure either to OGD for 10 min or to 40 μM NMDA for 5 min. The results are shown in FIG. 3.

The foregoing results demonstrate that there is an inverse correlation between an increased expression of UCP-2 and neuronal damage. Said differently, these results show that the expression pattern of UCP-2 correlates with a neuroprotected state of the brain during and following ischemia. These results indicate that agents that can increase the activity of UCP-2 are neuroprotective and can serve as therapeutic agents against stroke and other neurodegenerative diseases.

EXAMPLE 2

Neuroprotection by Overexpression of UCP-2 in Neurons Via a Recombinant UCP-2 Adenovirus I. Methods A. Generation of Recombinant UCP-2 Adenovirus Whole rat brain cDNA was used to obtain a PCR fragment containing a 930 nucleotide ORF (Open Reading Frame) corresponding to rat UCP-2. The PCR product was ligated to the T/A cloning vector pCR2.1 (Invitrogen, San Diego) and sequenced. Rat UCP-2 cDNA was then subcloned into the pShuttle-CMV transfer vector (Quantum Biotechnologies, Montreal). The resulting plasmid was linearized with Pme I and co-transformed into *E. coli* strain BJ183 together with pAdEasy-1, the viral DNA plasmid (Quantum Biotechnologies, Montreal). The pAdEasy-1 is E1 and E3 deleted, and its E1 functions can be complemented in 293 cells. Recombinants were selected with kanamycin and screened by restriction enzyme analysis. The recombinant adenoviral construct was then cleaved with PacI to expose its ITR (Inverted Terminal Repeats) and transfected into 293 cells to produce viral particles. A stock of 1012 VP/ml (Viral Particles per ml) of recombinant UCP-2 adenovirus was produced. Expression of recombinant rat UCP-2 driven by the strong CMV (CytoMegalo Virus) promoter was confirmed in infected 293 cells by Western blot analysis.

B. In vitro Functional Validation of UCP-2

Cell Culture.

Primary cortical neuronal cultures were prepared from gestational day 17 fetal rats. The cortex was dissected under a microscope, and the cells dissociated by trituration in modified Eagle's medium (MEM), 10% horse serum, 10% fetal bovine serum, 2 mM glutamine following a 30 min digestion in 0.027% trypsin/saline solution. Cells were plated in 6 mm multiwell (Nunc) plates coated with poly-ornithine at a density of $1-2\times10^5$ cells per well. Four days after plating, the cultures were treated with 10 µg/ml of 5-fluoro-2'-deoxyuridine for 3 days to inhibit proliferation of non-neuronal cells. Cultures were maintained in MEM, 5% horse serum, 2 mM glutamine in 8% $CO_2$, humidified, 37° C. atmosphere. The medium was changed twice a week. Mature neurons (12 days in vitro, DIV12) were used for all experiments. In mature cultures, neurons represent 70–90% of the total number of cells.

Infection of Neurons. Neurons were exposed to $2\times10^{10}$ VP/ml (an approximate multiplicity of infection of 20 virus particles per cell) of recombinant adenovirus containing rat UCP-2. An adenovirus expressing the lacZ gene driven by the same promoter (CMV) was used as control. DIV12 neuronal cultures were exposed to recombinant adenovirus in serum-free medium for 2 h at 37° C. During this incubation, cells were rocked gently every 15 minutes. After 2 h in serum-free medium, regular growth medium containing 5% horse serum was added to the cultures. Experiments were performed on infected cells 24 h after exposure to viral articles.

Ischemia. Combined oxygen-glucose deprivation (OGD) was performed 24 h after adenoviral infection of neurons by complete exchange of media with deoxygenated, glucose-free Earle's balanced salt solution (EBSS) containing 116 mM NaCl, 5.4 mM KCl, 0.8 mM $MgSO_4$, 1 mM $NaH_2PO_4$, and 0.9 mM $CaCl_2$, bubbled with 5% $H_2$/85% $N_2$/5% $CO_2$. The cultures were kept in an anaerobic chamber for 90 mm containing the gas mixture, 5% $H_2$/85% $N_2$/5% $CO_2$, maintained at 37° C. OGD was terminated by removal of the cultures from the chamber and replacement of the EBSS solution with oxygenated growth media.

Survival/Death Assay. Neuronal survival was assessed 24 h after OGD and presented as % cell death determined as the ratio of dead to live cells. Cell viability was determined by determination of fluorescence readings by a fluorescence plate reader after staining the nuclei of dead neurons with 8 µM of Ethidium Homodimer, and the cytoplasm of live cells by Calcein. For some treatment conditions, cell survival results were confirmed by an independent method using computer assisted cell counting after staining of all nuclei with 1 µg/ml Hoescht 33342 and dead cell nuclei with 7 µM propidium iodide. At least three independent experiments utilizing three separate wells per experiment were performed.

Western Blot Analysis. UCP-2 expression in rat primary neuronal cultures was analyzed by western blot. A total of 60 µg protein from each fraction was resolved on a 10–20% acrylamide gradient gel, blotted on nitrocellulose membrane and developed with an anti-UCP2 antibody, or anti MAP-2 antibody.

Immunofluorescence Analysis. Primary neurons were cultured on PDL coated coverslips and infected with Ad.UCP-2. A mitochondria-selective probe, MitoTracker green (250 nM, Molecular Probe, Eugene, Oreg.), was used for staining cells for 30 min at 37° C. in culture medium. After incubation with MitoTracker green, cells was washed in PBS, fixed with fresh made 4% paraformaldehyde in phosphate buffer solution (PBS) for 30 min at 37° C. and followed by permeabilization with 0.1% Triton X-100 for 3 min at 4° C. Fixed cells were blocked with 5% BSA, 0.1% Tween 20 in PBS for 1 hr at room temperature and incubated overnight at 4° C. with a monoclonal antibody (1:100, CALBIOCHEM, CA) that recognizes UCP-2. Following two washes with PBS, primary antibody was detected using Cy™ 3-conjugated anti-rabbit Ig G (1:100 Jackson ImmunoResearch Laboratories, Inc. PA). Neurons were mounted and examined with fluorescent microscope at magnification of 100× under oil immersion. Images were obtained with digital video camera system (Optronics, Goleta, Calif.).

II. Results

Figure 4:
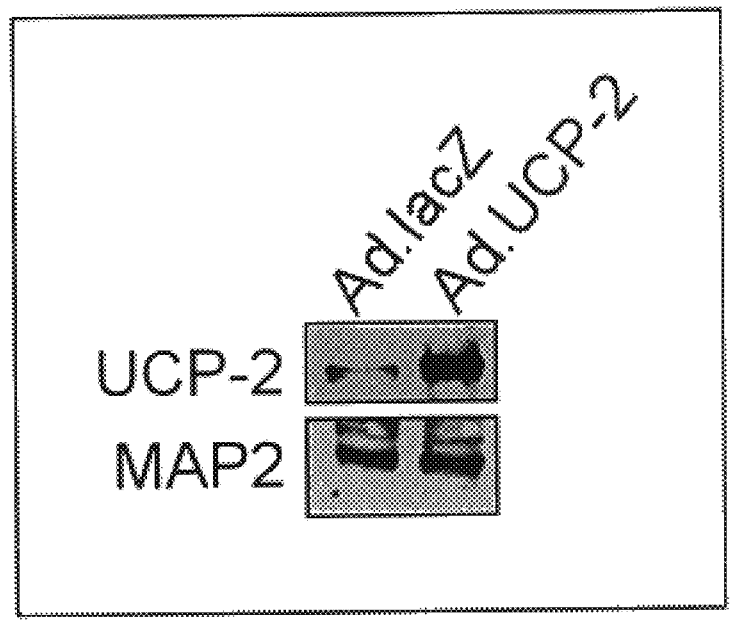
FIG. 4 shows western blot analysis of overexpression of recombinant UCP-2 in rat primary neuronal cultures by infection of neurons with an adenovirus containing a nucleic acid encoding UCP-2.

FIG. 4 shows results of western blot analysis of UCP-2 protein levels in rat primary cortical neuronal cultures. Twenty-four hours after infection with the recombinant adenovirus, UCP-2 protein levels were increased approximately 20-fold in Ad.UCP-2 exposed cultures compared to Ad.lacZ infected cultures. Probing with an anti-MAP2 antibody demonstrates equal protein loading.

Figure 5:
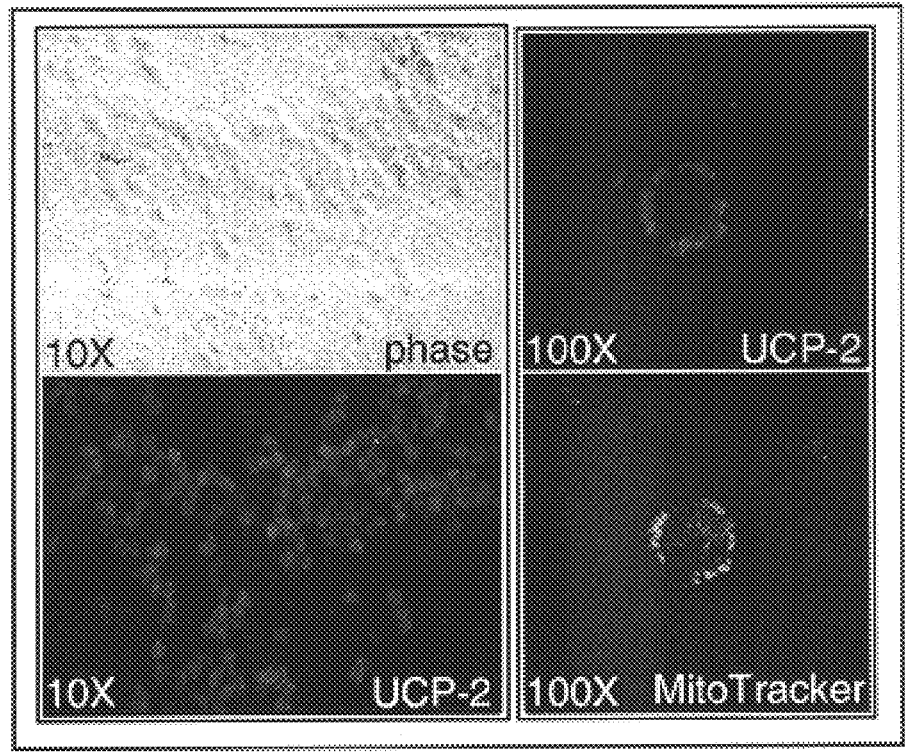
FIG. 5 shows immunofluorescence analysis of overexpression of recombinant UCP-2 in rat primary neuronal cultures.

Results of immunofluorescence analysis of UCP-2 recombinant expression in rat primary neuronal cultures are shown in FIG. 5. Cultures were infected with recombinant UCP-2 adenovirus and stained with an UCP-2 specific antibody (UCP-2), or a mitochondria-selective dye (MitoTracker). Images were taken at 10× and 100×magnification. The staining pattern indicates localization of UCP-2 protein in mitochondria.

Figure 6B:
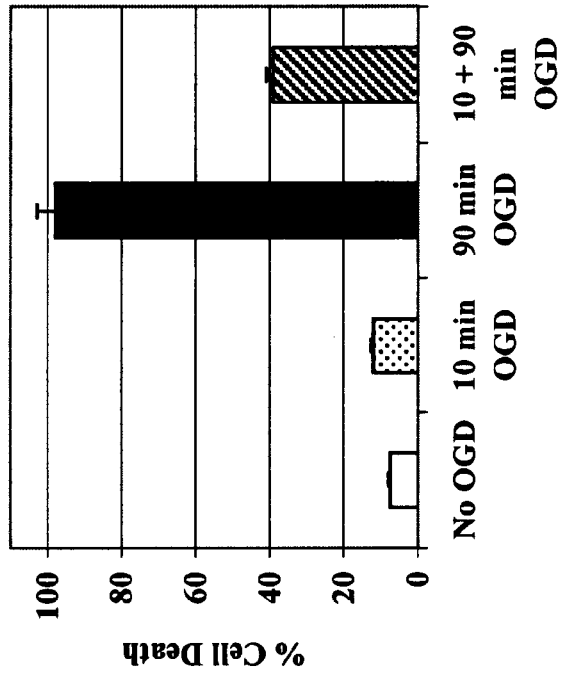
FIGS. 6A and 6B are plots illustrating the neuroprotective effect obtained by infection of neurons with an adenovirus containing a nucleic acid encoding UCP-2. Specifically, the plot illustrates protection of neuronal cultures against cell death induced by combined oxygen-glucose deprivation (OGD).
Figure 6A:
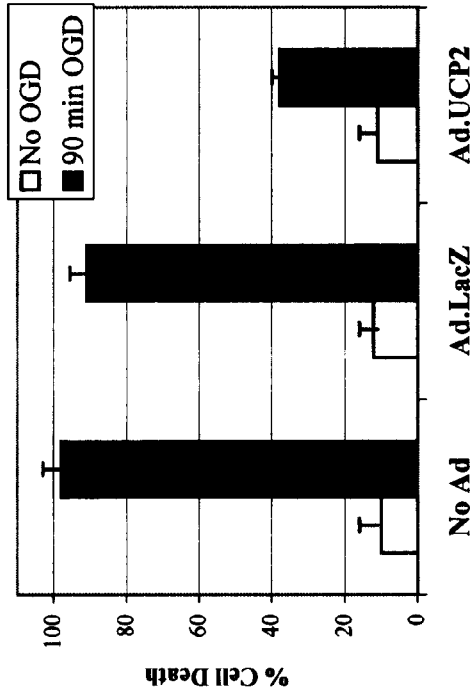

The effect of UCP-2 overexpression on neuronal death induced by OGD is shown in FIGS. 6A and 6B. To control against effects induced by the recombinant adenovirus system, the reporter lacZ gene was used. OGD induced over 90% neuronal death in cultures infected with lacZ adenovirus and in non-infected control cells (FIG. 6A). In contrast, neurons expressing recombinant UCP-2 were remarkably protected from OGD-induced damage since OGD caused death in only 48% of these cells. These results show that overexpression of UCP-2 confers 55–60% protection to neurons against OGD-induced death, suggesting a major role of UCP-2 as a neuroprotective protein against ischemia.

UCP-2 overexpression in cortical neuronal cultures confers a level of resistance (52% protection) to OGD-induced cell death that is very similar to the protection induced by ischemic preconditioning in vitro (59% protection) (FIG. 6B).

The above results indicate that UCP-2 and ischemic preconditioning may trigger common neuroprotective pathways, and further support the remarkable neuroprotective action of UCP-2 against neuronal loss induced by stroke, global ischemia and possibly other neuronal insults.

EXAMPLE 3

Reduction of Ischemic Brain Damage In Vivo by UCP-2 Overexpression

To examine effect of UCP-2 overexpression on ischemic brain damage in vivo, focal ischemia in mouse was induced by insertion of a 6-nylon suture coated with silicone into the middle cerebral artery under 2% halothane in a mixture of $N_2O/O_2$ (70/30) as described in Hara et al., *J. Cereb. Blood Flow Metab.* 16, 605 (1996), while the animal was spontaneously breathing through an open mask. The body temperature was kept at 36–38° C., and cortical blood flow was measured by laser Doppler flowmetry. Following 50 min occlusion, the nylon suture was removed. The wounds were sutured, and the animal was allowed to recover for 24 hr before being sacrificed. The brain was sectioned and stained red when tetrazolium trichloride is oxidized by mitochondria in viable tissue. The infarct was calculated as described in Kuroda et al., *J Cereb Blood Flow Metab* 19, 778 (1999).

Figure 7:
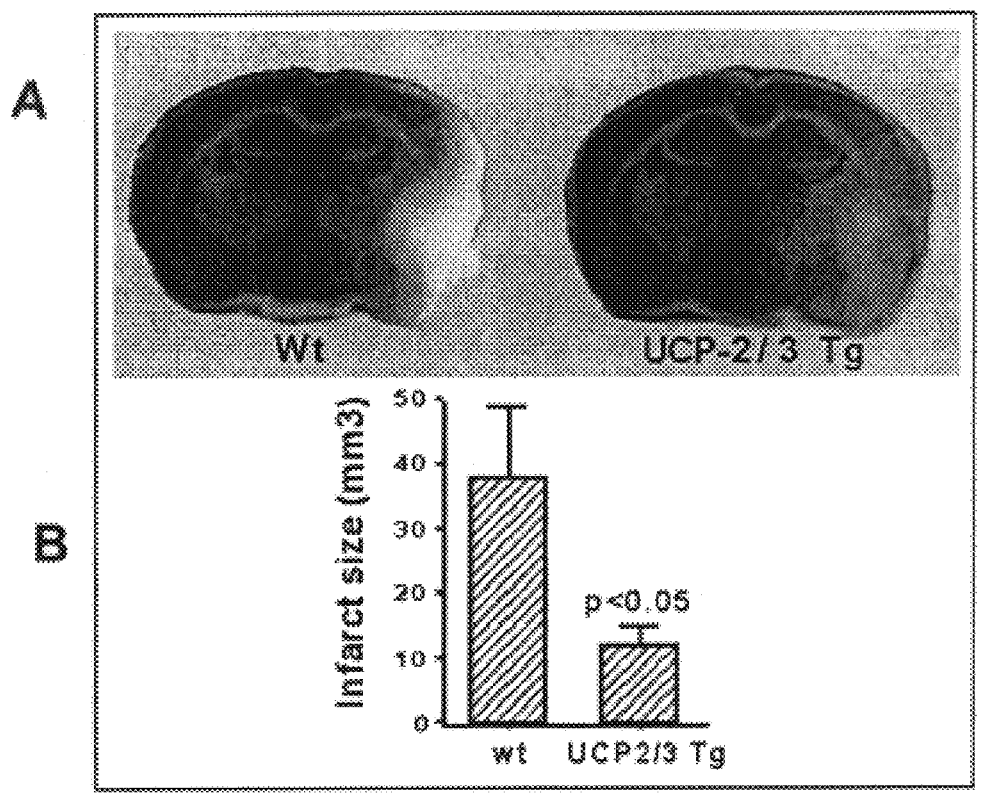
FIGS. 7A and 7B shows effects of UCP-2 overexpression on ischemic brain damage in vivo.

FIG. 7 shows ischemic brain damage induced by occlusion of the middle cerebral artery in wild-type mice (wt) and UCP-2/3 transgenic mice (UCP-2/3 Tg). White areas in the top panel indicate tissue damage. The data in the bottom panel represent the mean infarct size in mm³±SEM (Mann Whitney U test. n=9). The results demonstrate that UCP-2 overexpression results in smaller infract size, indicating reduced ischemic brain damage in vivo.

EXAMPLE 4

UCP-2 Regulation of Mitochondrial Permeability Transition, Release of Cytochrome C, and Caspase 3 Activation I. Methods Isolation of Brain Mitochondria and Analysis. Rat brain mitochondria were isolated as described in Xiong et al., *J. Neurotrauma.* 14, 23 (1997) with some modifications. Mouse cortex was homogenized in 320 mM sucrose, 1 mM EGTA, 10 mM Tris (pH 7,4) using a 2 ml Kontes Teflon homogenizer. The debris was then pelleted (2.000 g, 3 min, 4° C.). The supernatant was centrifuged (10.000 g, 10 min, 4° C.). The crude mitochondrial pellet was washed once in homogenization buffer. Respiratory activity of mitochondrial preparations was determined as described in Sims, *J. Neurochem.* 55, 698 (1990). Generation of free radical by mitochondria was measured using flow cytometric analysis in a FACSCalibur equipped with a 488 nm argon laser. The concentrations of fluorescent probes used did not affect RCR compared to control.

For analysis, mitochondria were suspended in 500 µl buffer (250 mM sucrose, 20 mM MOPS, 10 mM Tris-Base, 100 µM $P_i(K)$, 0.5 mM $Mg^{2+}$, pH 7.0) which also contains 5 mM succinate. To assess purity of the analysed gate, mitochondria were stained with 100 nM 10-nonyl-acridine orange (Mol. Probes, Oregon, USA). This gate was used for analysis of free radical generation by H2DCF-DA analysis (Teranishi et al., *Exp. Mol. Pathol.* 68, 104(2000). A total of 40 µg mitochondrial protein was resuspended in 500 µl of analysis buffer containing 5 mM succinate, 1 µM CsA either in the presence or in the absence of 10 µM H2DCFDA. H2DCFDA is converted to the fluorescent compound DCF upon reaction with ROS. The geometric mean fluorescence for each sample was calculated, and the background fluorescence for each sample was subtracted. The resulting value was compared between the two genotypes at different time points. Samples were analyzed in triplicate. At each time point, the mean fluorescence for each sample was calculated, and the control value (background) was subtracted.

Analysis of Mitochondrial Membrane Potential. Rat primary neuronal cultures were incubated with 2 µg/ml of JC-1 (Molecular Probes) for 20 min at 37C. Following incubation, cells were washed twice with 1×PBS and observed under a fluorescence microscope using a 475 nm excitation optical filter.

Western Blot Analysis of Mitochondria Proteins. Cytosolic and mitochondrial extracts from cultured rat primary cortical neurons were prepared using the ApoAlert Cell Fractionation Kit (Clontech) according to the manufacturer's instructions. A total of 60 µg protein from each fraction was resolved on a 10–20% acrylamide gradient gel, blotted on nitrocellulose membrane and developed with an anti-cytochrome c antibody (1:500, BD Pharmingen).

Caspase-3 Activity Assay. Caspase-3 activity assay was employed to study effect of overexpression of UCP-2 on apoptotic cascade. Caspase-3 activity was measured in whole cell lysates of cultured rat primary cortical neurons using the Caspase Assay Kit (Clontech) according to the manufacturer's instructions. The caspase-3 activation assay provides a simple means for assaying caspase-3 activity in mammalian cells. In this assay a fluorescent emission shift of 7-amino-4-trifluoromethyl coumarin (AFC) is detected after cleavage of the AFC-substrate conjugate by caspase 3. DEVD-AFC, usually emits blue light ($\lambda$max=400 nm). However, upon proteolytic cleavage of the substrate by caspase 3, free AFC fluoresces yellow-green at 505 nm. Generation of a recombinant UCP-2 adenovirus, cell culture conditions, infection of neuron cells, inducement of OGD and survival/death assays were performed as described in Example 2.

II. Results

Figure 8:
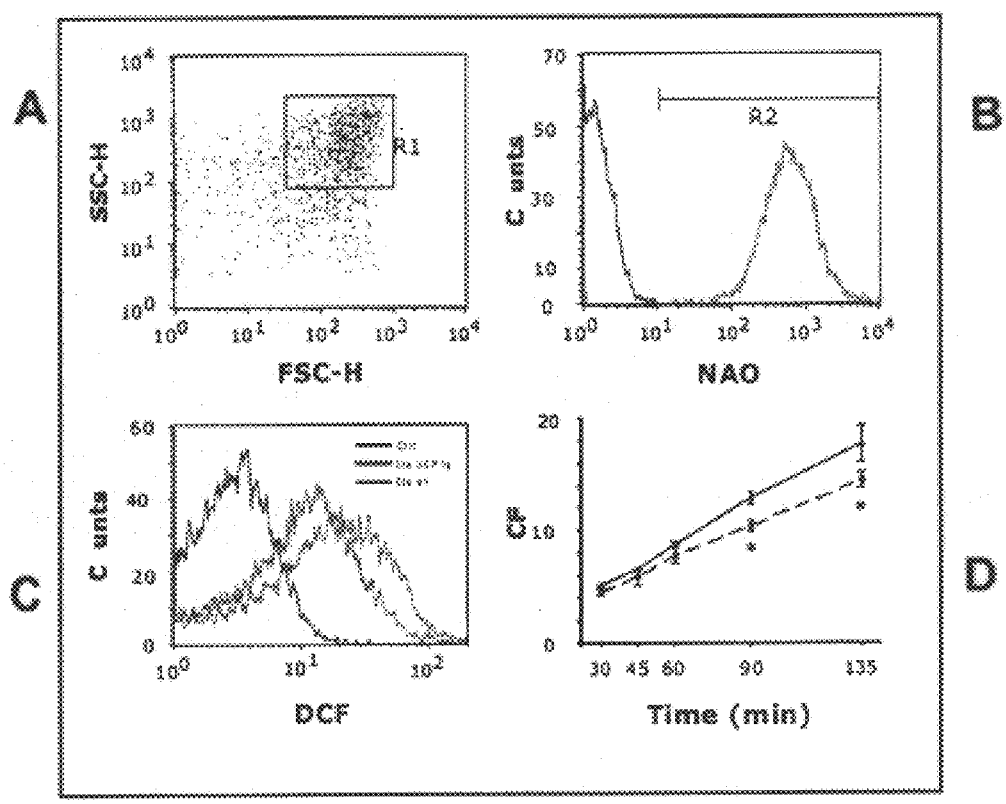
FIGS. 8A, B, C and D shows flow cytometry analysis of mitochondria isolated from rat brain cultures.

Isolated brain mitochondria were analyzed by flow cytometry as shown in FIG. 8. The upper left panel shows results plotted for side scattering (SSC) and forward scattering (FSC). Each dot represents one particle, and particles within area R1 were selected for analysis. Samples were stained with 100 nM 10-nonyl-acridine orange (NAO), a mitochondrial (cardiolipin) dye. As shown in the upper right panel, more than 98% of the events within gate R1 stain for NAO (right peak), suggesting that mainly mitochondria were analyzed (upper right:). The left peak in the upper right panel of FIG. 8 represents background sample fluorescence. The lower left panel of FIG. 8 shows generation of reactive oxygen species (ROS) in mitochondria isolated from cortex of UCP-2/3 Tg animals (middle peak) and wt animals (right peak) measured as formation of dichlorofluorescein (DCF) from H2DCF-diacetate. The left peak in this panel shows background fluorescence. The lower right panel shows the generation of ROS in brain cortex mitochondria from UCP-2/3 Tg animals (squares, dashed line) and wt animals (triangles, solid line) at 5 time points of incubation with H2DCF (lower right). The values were compared using an unpaired student's t-test (*=p<0.05).

The results indicate that overexpression of UCP-2 blocks OGD-induced mitochondrial membrane depolarization in rat primary cortical neuronal cultures. The cultures were infected with Ad.UCP-2 or Ad.lacZ, and 24 h later subjected to 90 min of OGD. Changes in the mitochondrial membrane potential were qualitatively assessed using the cationic fluorescent dye JC-1 at 8 h after OGD. Compared to Ad.lacZ infected cultures, cultures expressing Ad.UCP-2 displayed a higher red/green fluorescence ratio (data not shown), indicating preservation of the mitochondrial membrane potential.

Figure 9:
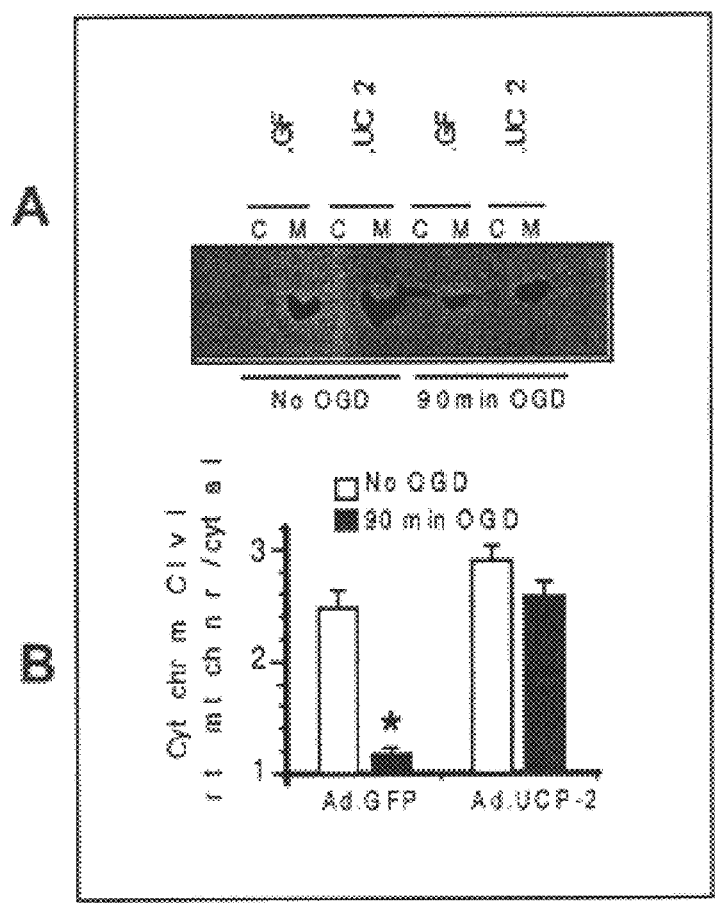
FIGS. 9A and 9B shows results of western blot analysis of cytochrome c protein levels in cytosolic and mitochondrial cell fractions.

Results of western blot analysis of cytochrome c protein levels in cytosolic and mitochondrial cell fractions are shown in FIG. 9. Rat primary cortical cultures were infected with Ad.UCP-2 or Ad.GFP, and 36 h later subjected to 90 min of OGD. Cytosolic (C) and mitochondrial (M) fractions were prepared 24 h after exposure to OGD, adjusted for protein concentration and subjected to immunoblot analysis using a cytochrome c specific antibody. The presence of cytochrome c in the cytosolic fraction after 90 min of OGD of Ad.GFP infected cells indicates that cell death involves mitochondrial release of cytochrome c into the cytosol. The bottom panel shows quantification of the western blot results and provides ratio of cytochrome c band intensity in the mitochondrial versus the cytosolic fraction for each condition. A lower ratio indicates release of cytochrome c from mitochondria into cytosol. The results indicate that UCP-2 overexpression reduces OGD-induced cytochrome c release from mitochondria. A total of 3 independent experiments showed similar results. Western blot results were confirmed by quantitative ELISA analysis using a Quantikine M Immunoassay kit from R&D Systems.

Activation of caspase 3 is a marker for apoptosis. To elucidate the mechanism by which UCP-2 generates its neuroprotective effect, tests were conducted to determine what effect overexpression of UCP-2 had on components of an apoptotic cascade. In particular, the effect of UCP-2 overexpression on the activity of caspase 3 was determined. This was done by testing the effect of UCP-2 overexpression on neuronal death induced by OGD using a recombinant adenovirus to achieve overexpression of UCP-2. An recombinant adenovirus having the lacZ gene instead of UCP-2 was used as a control.

Figure 10:
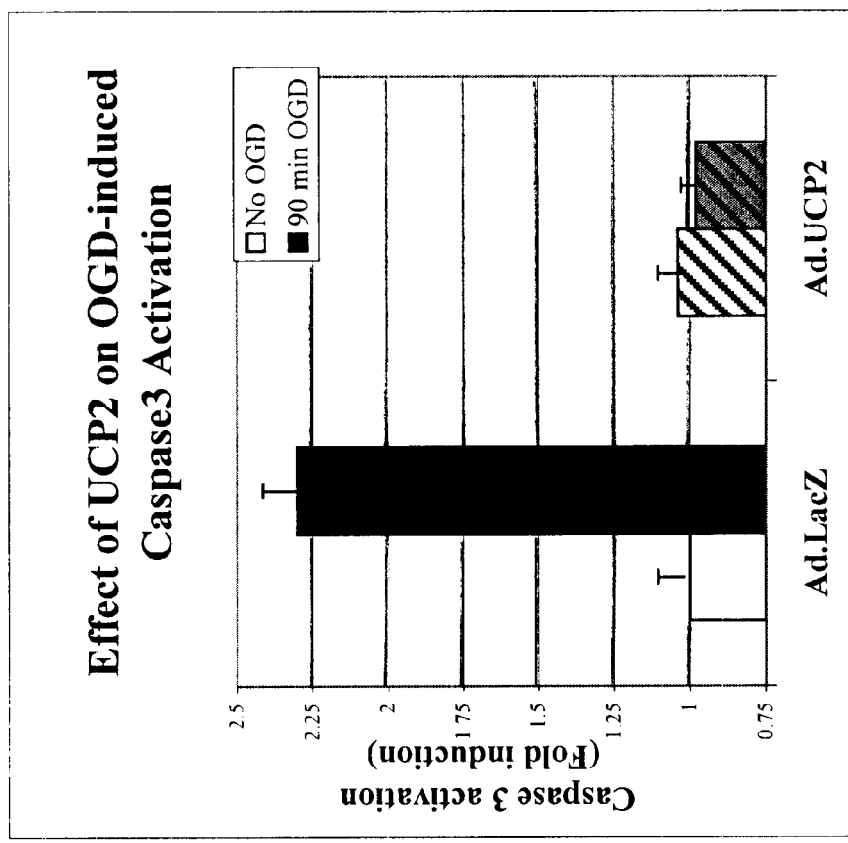
FIG. 10 is a chart showing the effect of UCP-2 expression on caspase 3 activation, with caspase 3 being induced by subjecting cell cultures to 90 min of OGD. Tests were performed with cells infected with an adenovirus having the lacZ gene instead of UCP-2 (Ad.LacZ; control) and cells infected with an adenovirus including the UCP-2 gene (Ad.UCP2).

FIG. 10 shows that overexpressed UCP-2 in cortical cultures blocks OGD-induced caspase 3 activation. The results strongly indicate that UCP-2 is neuroprotective by inhibition of apoptosis, including the blockade of caspase 3 activation by UCP-2. Programmed cell death, or apoptosis, requires activation of a series of cysteine proteases that specifically cleave target proteins after an aspartate residue.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method for diagnosing occurrence of neuronal exposure to hypoxia-ischemia comprising detecting in a patient's blood, serum, or cerebrospinal fluid sample an elevated level of UCP-2 polypeptide, wherein said elevated level of UCP-2 polypeptide is diagnostic of neuronal exposure to hypoxia-ischemia.

2. The method of claim 1, wherein said neuronal exposure to hypoxia-ischemia is an ischemic stroke.

3. The method according to claim 1, wherein said sample is cerebrospinal fluid.

4. The method of claim 1, wherein said detection comprises assaying for the presence of the UCP-2 polypeptide by contacting the sample with antibody that binds to the UCP-2 polypeptide to form a complex and detecting said complex.

5. The method of claim 4, wherein detection comprises performing an ELISA.

6. The method according to claim 1, comprising comparing the level of UCP-2 polypeptide in a test sample from the patient with a baseline value, wherein an elevated level of UCP-2 polypeptide in the patient sample relative to the baseline is diagnostic of neuronal exposure to hypoxia-ischemia.

7. The method of claim 6, wherein the baseline value is the level of UCP-2 expression in a patient sample obtained prior to the test sample.

8. The method of claim 6, wherein the baseline value is an average or mean value for UCP-2 expression in a population of control individuals.

* * * * *

SEQUENCE LISTING

<160> NUMBER OF SEQ ID NOS: 8

<210> SEQ ID NO 1
<211> LENGTH: 930
<212> TYPE: DNA
<213> ORGANISM: Unknown Organism
<220> FEATURE:
<223> OTHER INFORMATION: Description of Unknown Organism: Any animal
      source, typically mammalian, most typically human

<400> SEQUENCE: 1

```
atggttgggt tcaaggccac agatgtgccc cctactgcca ctgtgaagtt tcttggggct      60
ggcacagctg cctgcatcgc agatctcatc acctttcctc tggatactgc taaagtccgg     120
ttacagatcc aaggagaaag tcagggcca gtgcgcgcta cagccagcgc ccagtaccgc      180
ggtgtgatgg gcaccattct gaccatggtg cgtactgagg gcccccgaag cctctacaat     240
gggctggttg ccggcctgca gcgccaaatg agctttgcct ctgtccgcat cggcctgtat     300
gattctgtca aacagttcta caccaagggc tctgagcatg ccagcattgg gagccgcctc     360
ctagcaggca gcaccacagg tgccctggct gtggctgtgg cccagcccac ggatgtggta     420
aaggtccgat tccaagctca ggcccgggct ggaggtggtc ggagatacca aagcaccgtc     480
aatgcctaca agaccattgc ccgagaggaa gggttccggg gcctctggaa agggacctct     540
cccaatgttg ctcgtaatgc cattgtcaac tgtgctgagc tggtgaccta tgacctcatc     600
aaggatgccc tcctgaaagc caacctcatg acagatgacc tcccttgcca cttcatttct     660
gcctttgggg caggcttctg caccactgtc atcgcctccc ctgtagacgt ggtcaagacg     720
agatacatga actctgccct gggccagtac agtagcgctg gccactgtgc ccttaccatg     780
ctccagaagg aggggccccg agccttctac aaagggttca tgccctcctt tctccgcttg     840
ggttcctgga acgtggtgat gttcgtcacc tatgagcagc tgaaacgagc cctcatggct     900
gcctgcactt cccgagaggc tcccttctga                                      930
```

<210> SEQ ID NO 2
<211> LENGTH: 309
<212> TYPE: PRT
<213> ORGANISM: Unknown Organism
<220> FEATURE:
<223> OTHER INFORMATION: Description of Unknown Organism: Any animal
      source, typically mammalian, most typically human

<400> SEQUENCE: 2

Met Val Gly Phe Lys Ala Thr Asp Val Pro Pro Thr Ala Thr Val Lys
 1               5                  10                  15

```
Phe Leu Gly Ala Gly Thr Ala Ala Cys Ile Ala Asp Leu Ile Thr Phe
             20                  25                  30
Pro Leu Asp Thr Ala Lys Val Arg Leu Gln Ile Gln Gly Glu Ser Gln
         35                  40                  45
Gly Pro Val Arg Ala Thr Ala Ser Ala Gln Tyr Arg Gly Val Met Gly
     50                  55                  60
Thr Ile Leu Thr Met Val Arg Thr Glu Gly Pro Arg Ser Leu Tyr Asn
 65                  70                  75                  80
Gly Leu Val Ala Gly Leu Gln Arg Gln Met Ser Phe Ala Ser Val Arg
                 85                  90                  95
Ile Gly Leu Tyr Asp Ser Val Lys Gln Phe Tyr Thr Lys Gly Ser Glu
            100                 105                 110
His Ala Ser Ile Gly Ser Arg Leu Leu Ala Gly Ser Thr Thr Gly Ala
        115                 120                 125
Leu Ala Val Ala Val Ala Gln Pro Thr Asp Val Val Lys Val Arg Phe
    130                 135                 140
Gln Ala Gln Ala Arg Ala Gly Gly Gly Arg Arg Tyr Gln Ser Thr Val
145                 150                 155                 160
Asn Ala Tyr Lys Thr Ile Ala Arg Glu Glu Gly Phe Arg Gly Leu Trp
                165                 170                 175
Lys Gly Thr Ser Pro Asn Val Ala Arg Asn Ala Ile Val Asn Cys Ala
            180                 185                 190
Glu Leu Val Thr Tyr Asp Leu Ile Lys Asp Ala Leu Leu Lys Ala Asn
        195                 200                 205
Leu Met Thr Asp Asp Leu Pro Cys His Phe Ile Ser Ala Phe Gly Ala
    210                 215                 220
Gly Phe Cys Thr Thr Val Ile Ala Ser Pro Val Asp Val Val Lys Thr
225                 230                 235                 240
Arg Tyr Met Asn Ser Ala Leu Gly Gln Tyr Ser Ser Ala Gly His Cys
                245                 250                 255
Ala Leu Thr Met Leu Gln Lys Glu Gly Pro Arg Ala Phe Tyr Lys Gly
            260                 265                 270
Phe Met Pro Ser Phe Leu Arg Leu Gly Ser Trp Asn Val Val Met Phe
        275                 280                 285
Val Thr Tyr Glu Gln Leu Lys Arg Ala Leu Met Ala Ala Cys Thr Ser
    290                 295                 300
Arg Glu Ala Pro Phe
305

<210> SEQ ID NO 3
<211> LENGTH: 373
<212> TYPE: DNA
<213> ORGANISM: Artificial Sequence
<220> FEATURE:
<223> OTHER INFORMATION: Description of Artificial Sequence: SL3bE_F19
      clone

<400> SEQUENCE: 3
gatctgcagc cggactttgg cggtgtctag agggaaagtg atgaatctgc aatacaggct    60
gctgtcccag ccccaggaa cttcacgggt gggcttgtgg gggcacatc ggtgccttg    120 aaaccaacca tgattctgac ttcctgctac ctcccagaag atggagaaaa actgaagcag    180
tggggacctt caatcgtcaa gacgagacag aggaactctg ccggagtcgg gagggtgctt    240
tgaggtctca cgctgaaggc ctccaagatc aagcttctct aaaggtgtcc gttcttcaaa    300
```

```
gctgccagtg gctatcatgg cctgatcccc ttgaatttcc atagaaaaat gtctgggaag    360
acgaaacact taa                                                      373

<210> SEQ ID NO 4
<211> LENGTH: 352
<212> TYPE: DNA
<213> ORGANISM: Artificial Sequence
<220> FEATURE:
<223> OTHER INFORMATION: Description of Artificial Sequence:SL3bF_D20

<400> SEQUENCE: 4
tcatggtcat agctgttcac cgactttaaa cgagcccagc ggatcgccaa gaggatttaa     60
atcggcttag cgtggcgcgg ccgaggtcgg tgccctggga tcgcttgctt cttgggcagc    120
caccgccgcc gtcggaccta gccgtctgca ctcctgtgtt ctcctgtgta ttctcctgcg    180
gtccggacac aatagtatga tctttaagtg gttcggcttc ccagactttt ctatgggaaa    240
tcaaggggat caggccatga tagccactgg cagctttgaa gaacgggaca cctttagaga    300
agcttgatct tggaggcctc agcgtgagac ctcaaagcac cctcccgact cc            352

<210> SEQ ID NO 5
<211> LENGTH: 381
<212> TYPE: DNA
<213> ORGANISM: Artificial Sequence
<220> FEATURE:
<223> OTHER INFORMATION: Description of Artificial Sequence:SL3bC_M24
      clone

<400> SEQUENCE: 5
cggccgaggt gccgtctgca ctcctgtgtt ctcctgtgta ttctcctgcg gtccggacac     60
aatagtatga tctttaagtg tttcgtctcc cagacatttt ctatgggaaa tcaaggggat    120
caggccatga tagcccactg cagctttgaa gaacgggaca cctttagaga agcttgatct    180
tggaggcctc agcgtgagac ctcaaagcac cctcccgact ccggcagagt tcctctgtct    240
cgtcttgacg attgaaggtc cccactgctt cagttttttct ccatcttctg ggaggtagca    300
ggaagtcaga atcatggttg gtttcaaggc caccgatgtg ccccccacag ccaccgtgaa    360
gttcctgggg gctgggacag c                                             381

<210> SEQ ID NO 6
<211> LENGTH: 211
<212> TYPE: DNA
<213> ORGANISM: Artificial Sequence
<220> FEATURE:
<223> OTHER INFORMATION: Description of Artificial Sequence:
      SL3b_CP2_J11

<400> SEQUENCE: 6
cgggcaggta ctgggcgctg gcggcggtgc gcgctagccc ttgactctct ccttggatct     60
gcagccggac tttggcggtg tctagaggga aagtgatgag atctgcaata caggctgctg    120
tcccagcccc caggaacttc acggtggctg tgggggggcac atcggtggcc ttgaaaccaa    180
ccatgattct gacttcctgc tacctcccag a                                   211

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Oligo
      28 probe
```

```
<400> SEQUENCE: 7
ctctggcagg aacccagaga accgtggagt caaacagagc cagg            44

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Oligo
      33 probe

<400> SEQUENCE: 8
agaagtgaag tggcaaggga ggtcgtctgt catgaggttg gctt            44
```